United States Patent
Ruijtenbeek et al.

(10) Patent No.: US 9,075,061 B2
(45) Date of Patent: Jul. 7, 2015

(54) METHOD FOR DETERMINING THE ESTROGEN RECEPTOR STATUS OF BREAST CANCER

(75) Inventors: Robby Ruijtenbeek, Utrecht (NL); Maria Helena Hilhorst, Wageningen (NL); Arzu Umar, Rotterdam (NL); Johannes Albert Foekens, Capelle a/d IJssel (NL); Johannes Wilhelmus Maria Martens, Rotterdam (NL)

(73) Assignee: PamGene B.V., 's-Hertogenbosch (NL)

( * ) Notice: Subject to any disclaimer, the term of this patent is extended or adjusted under 35 U.S.C. 154(b) by 545 days.

(21) Appl. No.: 13/138,847

(22) PCT Filed: Apr. 12, 2010

(86) PCT No.: PCT/EP2010/054771
§ 371 (c)(1),
(2), (4) Date: Oct. 7, 2011

(87) PCT Pub. No.: WO2010/116002
PCT Pub. Date: Oct. 14, 2010

(65) Prior Publication Data
US 2012/0046199 A1  Feb. 23, 2012

(30) Foreign Application Priority Data
Apr. 10, 2009 (EP) .................... 09157817

(51) Int. Cl.
*C12Q 1/48* (2006.01)
*C40B 40/10* (2006.01)
*C40B 30/08* (2006.01)
*G01N 33/574* (2006.01)
*G01N 33/74* (2006.01)

(52) U.S. Cl.
CPC .......... *G01N 33/57415* (2013.01); *C12Q 1/485* (2013.01); *G01N 33/74* (2013.01); *G01N 2333/723* (2013.01); *G01N 2800/52* (2013.01)

(58) Field of Classification Search
None
See application file for complete search history.

(56) References Cited

U.S. PATENT DOCUMENTS

| 2003/0190689 A1 | 10/2003 | Crosby et al. |
| 2008/0108795 A1 * | 5/2008 | Guo et al. .................. 530/387.7 |
| 2008/0255243 A1 | 10/2008 | Petricoin et al. |

FOREIGN PATENT DOCUMENTS

| EP | 08154417.3 | * | 4/2008 |
| WO | WO 2008049930 A2 | * | 5/2008 |
| WO | WO 2009/014761 A2 | | 1/2009 |
| WO | WO 2009125019 A1 | * | 10/2009 |

OTHER PUBLICATIONS

Han, Xiaoming, et al "A quantitative peptide array for evaluation of protein kinase activity" Anal. Biochem., Jan. 1, 2008, 372(1), pp. 106-115.*
Hilhorst R et al., entitled "Peptide microarrays for detailed, high-throughput substrate identification, kinetic characterization, and inhibition studies on protein kinase A," Analytical Biochemistry 387, 2009, 150-161.
Lemeer S et al., entitled "Protein-Tyrosine Kinase Activity Profiling in Knock Down Zebrafish Embryos," PLoS One, Jul. 2007, Issue 7, e581, 1-6.
PCT Notification of Transmittal of the International Search Report and the Written Opinion of the International Searching Authority, or the Declaration issued by the European Patent Office in connection with PCT International Patent Application No. PCT/EP2010/054771, 16 pages. Sep. 2, 2010.
PCT Notification of Transmittal of the International Preliminary Report dated Jun. 27, 2011 from the European Patent Office in connection with PCT International Patent Application No. PCT/EP2010/054771, 9 pages.

* cited by examiner

*Primary Examiner* — Jon P Weber
*Assistant Examiner* — Aaron J Kosar
(74) *Attorney, Agent, or Firm* — Amster, Rothstein & Ebenstein LLP

(57) ABSTRACT

The present invention relates to a method for determining the estrogen receptor status of patients suffering from breast cancer. The present invention also aims to provide methods and devices for predicting the response of patients diagnosed with breast cancer to specific medicaments. More specifically, the present invention provides methods which measure kinase activity by studying phosphorylation levels and profiles in samples obtained from patients diagnosed with breast cancer.

11 Claims, 3 Drawing Sheets

METHOD FOR DETERMINING THE ESTROGEN RECEPTOR STATUS OF BREAST CANCER

CROSS-REFERENCE TO RELATED APPLICATIONS

This application is a U.S. national stage entry under 35 U.S.C. §371 of PCT International Patent Application No. PCT/EP2010/054771, filed Apr. 12, 2010, and claims priority to European Patent Application No. 09157817.9 filed Apr. 10, 2009, the contents of which are incorporated herein by reference in their entirety.

FIELD OF THE INVENTION

The present invention relates to a method for determining the estrogen receptor status of patients suffering from breast cancer. The present invention also aims to provide methods and devices for predicting the response of patients diagnosed with breast cancer to specific medicaments. More specifically, the present invention provides methods which measure kinase activity by studying phosphorylation levels and profiles in samples obtained from patients diagnosed with breast cancer.

BACKGROUND OF THE INVENTION

Breast cancer is a cancer that starts in the cells of the breast in women and men. Worldwide, breast cancer is the second most common type of cancer after lung cancer (about 10% of all cancer incidences) and the fifth most common cause of cancer death.

Due to the high impact of breast cancer an early diagnosis of breast cancer is essential, especially since this improves the survival rate of breast cancer patients. Therefore in breast cancer, regular mammography and early diagnosis is of high importance. This increases the chances that the lymph nodes are not infiltrated, that the tumor can be surgically removed and local or regional therapy (radiation therapy) is sufficient.

In many cases of early and advanced breast cancer local or regional treatment is insufficient. In those cases, establishing the second line therapy most suited for each breast cancer patient is essential. After removal of (part) of the breast, systemic treatment like chemotherapy or targeted therapy is used. With new drugs, especially those targeting kinases, selection of patients using molecular diagnostics appears to be critical for success. Biomarkers like the estrogen receptor (ER), the progesterone receptor (PR) or the human epidermal growth factor receptor 2 (HER2) play an important role in deciding whether hormone therapy, Herceptin or another drug is included in the treatment of choice.

Determining the type of breast cancer is therefore important for providing the most suited treatment of the patient. It is known that for early and advanced breast cancer both in pre- and postmenopausal women, Tamoxifen or another anti-estrogen like raloxifene, lasofoxifene or bazedoxifene, is a suited treatment for an estrogen receptor positive (ER+) and/or an progesterone receptor positive (PR+) breast tumor. Tamoxifen is an anti-estrogen from the group of SERMs (Selective Estrogen Receptor Modulator). Recently, aromatase inhibitors have become the drugs of choice for treatment of breast cancer in postmenopausal ER+ or PR+ women. Aromatase inhibitors prevent the formation of estrogens by inhibition of enzymes that catalyze the conversion of androsterons to estrogen. By blocking the action of the enzyme aromatase, no more estrogens are produced in the body.

Human epidermal growth factor receptor 2 positive (HER2+) breast cancer is currently treated with Herceptin. For breast tumors that are estrogen receptor negative, progesterone receptor negative and HER2 negative, no targeted therapy is available and in general prognosis is poor.

For determining whether a breast tumor is either ER positive or negative, HER2 positive or negative and/or PR positive or negative usually immunohistochemical, PCR or FISH methods are used. These methods localize the estrogen, human epidermal growth factor or progesterone receptors in the tumor cells using antibodies binding specifically to the estrogen, human epidermal growth factor or progesterone receptors. However, these immunohistochemical measurements are not well standardized yet and their reliability to predict hormone therapy responses is limited.

The presence of estrogen receptors is the best indicator of response to anti-estrogen agents such as tamoxifen. However, 30% to 40% of women with estrogen receptor positive breast cancer will develop distant metastases and die despite tamoxifen treatment, which percentage is even higher for ER+ PR− (60%).

Consequently, there remains need for methods that provide a fast and accurate measurement of the estrogen, human epidermal growth factor or progesterone receptor status in breast tumors. These methods would enable the identification of the type of breast cancer at an early stage, and more specifically provide an early determination of the most suited treatment of the breast cancer patient.

The present invention aims at providing methods and devices for determining the estrogen receptor status of patients suffering from breast cancer. The present invention also aims to provide methods and devices for predicting the response of patients diagnosed with breast cancer to specific medicaments. The method of the present invention therefore adds to the existing HER2, ER and PR immunohistochemical assays currently used to select therapies in breast cancer patients.

SUMMARY OF THE INVENTION

The present invention provides methods and devices that enable the determination of the estrogen receptor status of patients suffering from breast cancer based on the measurement of the kinase activity of a breast tumor sample. The present invention further shows how the method and devices can be used to predict the response of patients diagnosed with breast cancer to specific medicaments.

The inventors show that kinase activity profiling of breast tissue lysates can provide a new and improved method to predict endocrine treatment efficacy in breast cancer patients since it measures the activities of endocrine therapy relevant signalling pathways.

The present invention therefore provides a method for determining the estrogen receptor status of a breast tumor. In a first embodiment of the present invention, the method comprises the steps of:

(a) measuring kinase activity of a sample from said breast tumor, thereby providing a phosphorylation profile of said sample; and, (b) determining from said phosphorylation profile the estrogen receptor status of said breast tumor.

In another embodiment according to the present invention, the phosphorylation profiles comprise the phosphorylation levels of, preferably one or more, phosphorylation sites present in at least any of the peptide markers as listed in table 1.

Another embodiment of the present invention relates to a method for predicting the response of a patient, diagnosed with breast cancer, to a medicament, wherein the kinase activity of a sample, obtained from the breast tumor, is measured in the presence and in the absence of said medicament and wherein said kinase activity in the presence of said medicament is compared to the kinase activity in the absence of said medicament thereby determining the response of said patient to said medicament, wherein said kinase activity measurement provides phosphorylation profiles of said sample in the presence and in the absence of said medicament.

The present invention also relates according to another embodiment to an array for carrying out the method of the present invention, said array comprising immobilized proteins, peptides or peptide mimetics comprising, preferably one or more, phosphorylation sites present in any of the peptide markers as listed in table 1, wherein said proteins, peptides or peptide mimetics are preferably at least 25% of proteins, peptides or peptide mimetics on said array.

The present invention further relates in yet another embodiment to a method for determining the estrogen receptor status of a breast tumor, comprising the steps of:

(a) measuring the kinase activity of a sample, obtained from the breast tumor, in the presence and in the absence of a protein kinase inhibitor, thereby providing a phosphorylation profile of said sample; and, (b) determining from said phosphorylation profile the estrogen receptor status of said breast tumor.

These and further aspects and embodiments are described in the following sections and in the claims.

DETAILED DESCRIPTION OF THE INVENTION

Figure 1:
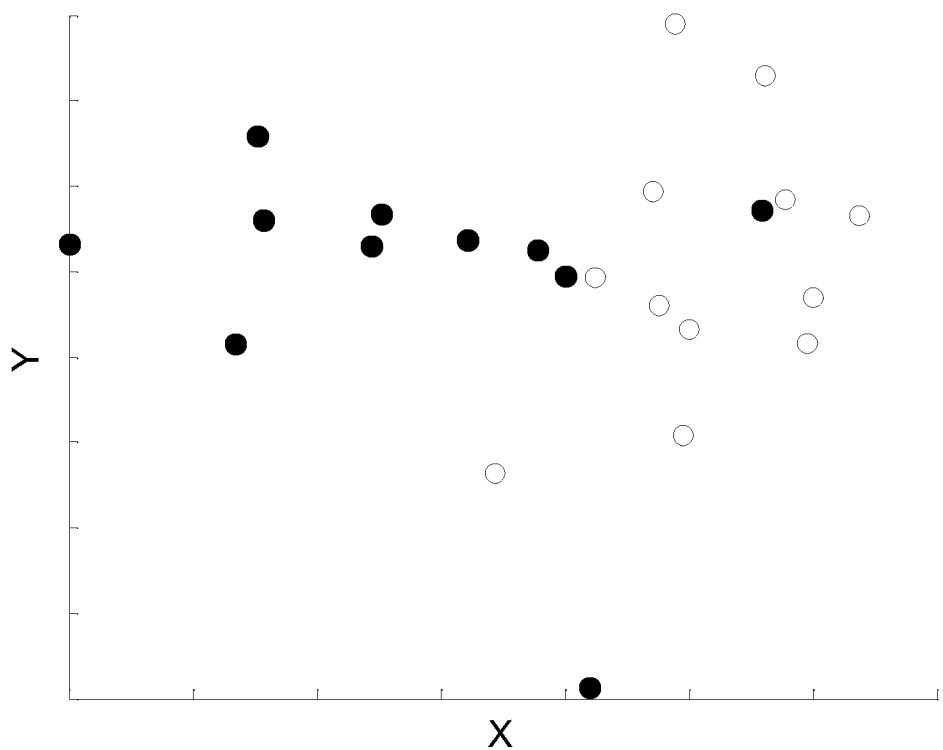
FIG. 1 provides, as depicted in the examples, a graphical representation of the scores on the 4th principal component (PC) on the X-axis and that of the fifth PC on the Y axis, each point represents one of the 23 samples, filled circles represent ER negative samples and open circles represent ER positive samples.

Before the present method and devices used in the invention are described, it is to be understood that this invention is not limited to particular methods, components, or devices described, as such methods, components, and devices may, of course, vary. It is also to be understood that the terminology used herein is not intended to be limiting, since the scope of the present invention will be limited only by the appended claims.

Unless defined otherwise, all technical and scientific terms used herein have the same meaning as commonly understood by one of ordinary skill in the art to which this invention belongs. Although any methods and materials similar or equivalent to those described herein may be used in the practice or testing of the present invention, the preferred methods and materials are now described.

In this specification and the appended claims, the singular forms "a", "an", and "the" include plural references unless the context clearly dictates otherwise.

The terms "comprising", "comprises" and "comprised of" as used herein are synonymous with "including", "includes" or "containing", "contains", and are inclusive or open-ended and do not exclude additional, non-recited members, elements or method steps.

The terms "comprising", "comprises" and "comprised of" also include the term "consisting of".

The term "about" as used herein when referring to a measurable value such as a parameter, an amount, a temporal duration, and the like, is meant to encompass variations of +/−10% or less, preferably +/−5% or less, more preferably +/−1% or less, and still more preferably +/−0.1% or less of and from the specified value, insofar such variations are appropriate to perform in the disclosed invention. It is to be understood that the value to which the modifier "about" refers is itself also specifically, and preferably, disclosed.

The recitation of numerical ranges by endpoints includes all numbers and fractions subsumed within the respective ranges, as well as the recited endpoints.

The present invention provides methods and devices that enable the determination of the estrogen receptor status for patients suffering from breast cancer based on the measurement of the kinase activity of a breast tumor sample. The present invention further shows how the method and devices can be used to predict the response of patients diagnosed with breast cancer to specific medicaments. The method of the present invention therefore adds to the existing HER2, ER and PR immunohistochemical assays currently used to select therapies in breast cancer patients.

Preferably, in one embodiment of the present invention, methods are provided wherein the kinase activity is protein kinase activity. For purposes of the present invention, and as used herein the term "enzyme activity", "kinase activity" or "protein kinase activity" refer to the formation of reaction product(s) by a certain amount of enzyme, kinase or protein kinase acting on a substrate during the course of the assay.

Protein kinase activity is referred to as the activity of protein kinases. A protein kinase is a generic name for all enzymes that transfer a phosphate to a protein. About three to four percent of the human genome contains transcription information for the formation of protein kinases. Currently, there are about 518 known different protein kinases. However, because three to four percent of the human genome is a code for the formation of protein kinases, there may be many more separate kinases in the human body.

A protein kinase is a kinase enzyme that modifies other proteins by chemically adding phosphate groups to them. This process or activity is also referred to as phosphorylation. Phosphorylation can therefore be regarded as the process of the addition of a phosphate group to a substrate. Phosphorylation usually results in a functional change of the substrate by changing enzyme activity, cellular location, or association with other proteins. Up to 30% of all proteins may be modified by kinase activity, and kinases are known to regulate the majority of cellular pathways, especially those involved in signal transduction, the transmission of signals within the cell. The chemical activity of a kinase involves removing a phosphate group from ATP or GTP and covalently attaching it to amino acids such as serine, threonine, tyrosine, histidine, aspartic acid and/or glutamic acid that have a free hydroxyl group. Most known kinases act on both serine and threonine, others act on tyrosine, and a number act on all serine, threonine and tyrosine. The protein kinase activity monitored with the method of the present invention is preferably directed to protein kinases acting towards serine, threonine and/or tyrosine, preferably acting on both serine and threonine, on tyrosine or on serine, threonine and tyrosine and more preferably the method of the present invention if preferably directed to protein kinases acting towards tyrosines.

Protein kinases are distinguished by their ability to phosphorylate substrates on discrete sequences. These sequences have been determined by sequencing the amino acids around the phosphorylation sites and are usually distinct for each protein kinase. The recognition sequence on each substrate is specific for each kinase catalyst.

Because protein kinases have profound effects on a cell, their activity is highly regulated. Kinases are turned on or off by for instance phosphorylation, by binding of activator proteins or inhibitor proteins, or small molecules, or by controlling their location in the cell relative to their substrates. Deregulated kinase activity is a frequent cause of disease, particularly cancer, where kinases regulate many aspects that control cell growth, movement and death. Therefore monitoring the protein kinase activity in tissues can be of great importance and a large amount of information can be obtained when comparing the kinase activity of different tissue samples.

As described in the present invention, the inventors have surprisingly found that the estrogen receptor status of patients suffering from breast cancer can be predicted and/or determined on the basis of the measurement of the kinase activity of a breast tumor sample.

The measurement of the kinase activity is performed by contacting a breast tumor sample with one or more substrates, preferably protein kinase substrates, thereby generating a phosphorylation profile.

Said protein kinase substrates as used herein, are preferably peptides, proteins or peptide mimetics. The protein kinase substrates each comprise, preferably one or more, phosphorylation sites that can be phosphorylated by the protein kinases present in the sample. Therefore, exposure of a protein kinase substrate to a sample comprising a protein kinase results in the phosphorylation of one or more of the phosphorylation sites of the protein kinase substrate. This phosphorylation activity can be measured using techniques known in the art. Therefore, during the measurement method the kinase enzymes present in the sample will phosphorylate, preferably one or more, of the phosphorylation sites on one or more protein kinase substrates. The inventors have observed essential differences between the kinase activity of breast tumors having a different estrogen receptor status. Consequently, the inventors have observed that the kinases present in a breast tumor sample will phosphorylate different protein kinase substrates depending on the estrogen receptor status of said breast tumors.

The present invention therefore provides a method for determining the estrogen receptor status of a breast tumor. In a first embodiment of the present invention, the method comprises the steps of:

(a) measuring the kinase activity of a sample from said breast tumor, thereby providing a phosphorylation profile of said sample; and, (b) determining from said phosphorylation profile the estrogen receptor status of said breast tumor.

As referred to in the present application breast cancer regards a malignant cancerous growth that begins in the tissues of the breast. Cancer is a disease in which abnormal cells grow in an uncontrolled way. The most common types of breast cancer are ductal carcinoma and lobular carcinoma. Ductal carcinoma refers to a condition where ductal cancer cells grow only inside the ducts of the breast. It is often referred to as a precancerous condition. Lobular carcinoma refers to a condition wherein the hollow glands or lobules where milk accumulates in the breast fill with abnormal cells. This is a precancerous condition and does not directly lead to breast cancer. About 86% of breast cancers are ductal carcinoma, about 12% belong to the lobular group. Paget's disease, originating in the nipple, is a rare from of breast cancer.

As used in the present invention, the term "sample" refers to a sample obtained from an organism (patient) such as human or from components (e.g. tissue or cells) of such an organism. Said sample is preferably obtained from a patient diagnosed with breast cancer and needs to be derived from the tumor tissue of said patient. More preferably said sample is a breast tumor tissue biopsy, fine needle biopsy, fine needle aspiration biopsy, core needle biopsy, vacuum assisted biopsy, open surgical biopsy or material from a resected tumor. Said sample is thereby referred to as a 'clinical sample' which is a sample derived from a breast cancer patient.

Said tumor tissue sample is preferably a fresh or a fresh frozen sample.

More preferably, said sample refers to a lysate of a breast tumor tissue obtained through tumor tissue biopsy, fine needle biopsy, fine needle aspiration biopsy, core needle biopsy, open surgical biopsy or material from a resected tumor. Alternatively said sample may be obtained from specific breast tumor cell lines and in particular cell lysates thereof.

Alternatively said sample may be derived from a tumor sample that has been cultured in vitro for a limited period of time.

In a preferred embodiment of the present invention said sample is a sample that has undergone a preparation step prior to the steps according to the method of the present invention. Preferably said preparation step is a step where the protein kinases present in said sample are released from the tissue by lysis. Additionally the kinases in the sample may be stabilized, maintained, enriched or isolated, and the measurement of the kinase activity as performed in step (a) occurs on the enriched or isolated protein kinase sample. By first enriching protein kinases in the sample or isolating protein kinases from the sample the subsequent measurement of the kinase activity will occur in a more efficient and reliable manner. Also the clarity and intensity of the obtained phosphorylation signal will be increased as certain contaminants are being removed during the enriching or isolating step.

As used in the present invention, the term "phosphorylation profile" refers to a data set representative for the phosphorylation levels of, preferably one or more, phosphorylation sites present on the protein kinase substrates. When measuring the kinase activity of a sample by contacting said sample with protein kinase substrates a specific phosphorylation profile is obtained. The phosphorylation profile is generated by the phosphorylation of the protein kinase substrates with the protein kinases present in the sample and it comprises the level of phosphorylation of the phosphorylation sites present on the protein kinase substrates used. A phosphorylation profile can thus be generated when using at least one protein kinase substrate in different test conditions such as for example by comparing the phosphorylation of a sample on one peptide or protein (protein kinase substrate) in the presence and absence of a protein kinase inhibitor. More frequently phosphorylation profiles of a sample will be measured using several protein kinase substrates in the same or sequentially carried out experiments. Preferably, the present invention determines tyrosine kinase activity levels or profiles.

It should be noted that a person skilled in the art will appreciate that the methods of the present invention can use phosphorylation profiles as a basis for determining the estrogen receptor status of a breast tumor. However, the phosphorylation levels of individual protein kinase substrates can also be used as a basis for determining the estrogen receptor status of a breast tumor.

It should be noted that for the measurement of the protein kinase activity, ATP, or any other phosphate source, needs to be added to the sample when it is contacted with the protein kinase substrates. The presence of ATP will lead to a phosphorylation of the protein kinase substrates. Alternatively, the phosphorylation of the protein kinase substrates can be performed in the absence of exogenous ATP. When no ATP is added during the incubation of the sample with the protein kinase substrates, the endogenous ATP, the ATP naturally present in the sample, will act as the primary source of ATP.

The phosphorylation level of each of the protein kinase substrates can be monitored using any method known in the art. The response of the protein kinase substrates is determined using a detectable signal, said signal resulting from the interaction of the sample with the protein kinase substrates or by for instance measuring mass differences using mass spectrometry. In determining the interaction of the sample with the protein kinase substrates the signal is the result of the interaction of the phosphorylated substrates with a molecule capable of binding to the phosphorylated substrates. This binding can be detected by e.g. surface plasmon resonance or by the molecule being detectably labelled. For the latter, the molecule that specifically binds to the substrates of interest (e.g. antibody or polynucleotide probe) can be detectably labelled by virtue of containing an atom (e.g. radionuclide), molecule (e.g. fluorescein), or enzyme or particle or complex that, due to a physical or chemical property, indicates the presence of the molecule. A molecule may also be detectably labelled when it is covalently bound to or otherwise associated with a "reporter" molecule (e.g. a biomolecule such as an enzyme) that acts on a substrate to produce a detectable atom, molecule or other complex.

Detectable labels suitable for use in the present invention include any composition detectable by spectroscopic, photochemical, biochemical, immunochemical, electrical, optical or chemical means. Labels useful in the present invention include biotin for staining with labelled avidin or streptavidin conjugate, magnetic beads (e.g. Dynabeads'), fluorescent dyes (e.g. fluorescein, fluorescein-isothiocyanate (FITC), Texas red, rhodamine, green fluorescent protein, enhanced green fluorescent protein and related proteins with other fluorescence emission wavelengths, lissamine, phycoerythrin, Cy2, Cy3, Cy3.5, Cy5, Cy5.5, Cy7, FluorX [Amersham], SYBR Green I & II [Molecular Probes], and the like), radiolabels (e.g. 3H, 125I, 35S, 4C, or 32P), enzymes (e.g. hydrolases, particularly phosphatases such as alkaline phosphatase, esterases and glycosidases, or oxidoreductases, particularly peroxidases such as horse radish peroxidase, and the like), substrates, cofactors, chemilluminescent groups, chromogenic agents, and colorimetric labels such as colloidal gold or coloured glass or plastic (e.g. polystyrene, polypropylene, latex, etc.), protein particles or beads.

Means of detecting such labels are well known to those of skill in the art. Thus, for example, chemiluminescent and radioactive labels may be detected using photographic film or scintillation counters, and fluorescent markers may be detected using a photodetector to detect emitted light (e.g. as in fluorescence-activated cell sorting). Enzymatic labels are typically detected by providing the enzyme with a substrate and detecting a coloured reaction product produced by the action of the enzyme on the substrate. Colorimetric labels are detected by simply visualizing the coloured label. Thus, for example, where the label is a radioactive label, means for detection include a scintillation counter, photographic film as in autoradiography, or storage phosphor imaging. Where the label is a fluorescent label, it may be detected by exciting the fluorochrome with the appropriate wavelength of light and detecting the resulting fluorescence. The fluorescence may be detected visually, by means of photographic film, by the use of electronic detectors such as charge coupled devices (CCDs) or photomultipliers and the like. Similarly, enzymatic labels may be detected by providing the appropriate substrates for the enzyme and detecting the resulting reaction product. Also, simple colorimetric labels may be detected by observing the colour associated with the label. Fluorescence resonance energy transfer has been adapted to detect binding of unlabeled ligands, which may be useful on arrays.

In a particular embodiment of the present invention the response of the protein kinase substrates to the sample is determined using detectably labelled antibodies; more in particular fluorescently labelled antibodies. In those embodiments of the invention where the substrates consist of protein kinase substrates, the response of the protein kinase substrates is determined using fluorescently labelled anti-phosphotyrosine antibodies, fluorescently labelled anti-phosphoserine or fluorescently labelled anti-phosphothreonine antibodies. The use of fluorescently labelled anti-phosphotyrosine antibodies or fluorescently labelled anti-phosphoserine or fluorescently labelled anti-phosphothreonine antibodies in the method of the present invention, allows real-time or semi real-time determination of the protein kinase activity and accordingly provides the possibility to express the protein kinase activity as the initial velocity of protein kinase derived from the activity over a certain period of incubation of the sample on the protein kinase substrates.

The inventors have found that measuring the kinase activity of a breast tumor sample, enables a differentiation between the estrogen receptor status of breast tumors. Compared to existing immunohistochemical methods the methods of the present invention have been found to be more relevant. This surprising effect is due to the fact that the measurement method according to the present invention is directed towards the signalling pathway of the estrogen receptor, and not the receptor itself. This enables an alternative determination of the estrogen receptor status of a breast tumor. Moreover, because the method of the present invention is based on the measurement of a number of protein kinase substrates the efficiency of the method increases significantly.

The statistical analysis of the phosphorylation profiles and levels can be done using multivariate and/or univariate statistical methods known in the art.

In addition, because the phosphorylation profile is generated by comparing the phosphorylation levels of a number of protein kinase substrates, the phosphorylation profile is surprisingly found to be less affected by variation, for example biological variation, experimental variation, compared to other types of profiles. This provides a more robust, more sensitive, more reproducible and more reliable method for determining the estrogen receptor status of a breast tumor.

In another embodiment according to the present invention, the phosphorylation profiles comprise the phosphorylation levels of, preferably one or more, phosphorylation sites present in at least any of the peptide markers as listed in table 1. Preferably phosphorylation levels will be studied of phosphorylation sites present in at least 2, 3, 4, 5, 6, 7, 8, 9 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, or 77 of the peptide markers listed in Table 1.

The term "peptide markers" in the context of the present invention refers to the fact that the peptides as listed in Table 1 can be preferably used according to the methods of the present invention to measure the phosphorylation levels of phosphorylation sites of said markers in the presence of protein kinase present in samples. The phosphorylation levels of the individual phosphorylation sites present in said markers may be measured and compared in different ways. Therefore the present invention is not limited to the use of peptides identical to any of these peptide markers as listed in Table 1 as such. The skilled person may easily on the basis of the peptide markers listed in Table 1 design variant peptides compared to the specific peptides in said Table and use such variant peptides in a method for measuring phosphorylation levels of phosphorylation sites common to said peptide markers as listed in Table 1. These variant peptides may have one or more (2, 3, 4, 5, 6, 7, etc.) amino acids more or less than the given peptides and may also have amino acid substitutions (preferably conservative amino acid substitutions) as long as these variant peptides retain at least, preferably one or more, of the phosphorylation sites of said original peptides as listed in said table. Further the skilled person may also easily carry out the methods according to the present invention by using proteins (full length or N- or C-terminally truncated) comprising the amino acid regions of the "peptide markers" listed in Table 1 as sources for studying the phosphorylation of sites present in the amino acid regions of the peptides listed in Table 1. Also the skilled person may use peptide mimetics.

The protein kinase substrates as used in the methods described herein, are meant to include peptides, proteins or peptide mimetics comprising, preferably one or more, of the phosphorylation sites of the peptide markers of Table 1. Said, preferably one or more, phosphorylation sites are specifically phosphorylated by the protein kinases present in the sample thereby providing a phosphorylation profile. More preferably the protein kinase substrates (peptides, proteins or peptide mimetics) as used in the method of the present invention comprise, preferably one or more, of the phosphorylation sites present in at least two peptide markers as listed in Table 1. More particularly said protein kinase substrates represent the, preferably one or more, phosphorylation sites present in at least 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, or 77 peptide markers as listed in Table 1. In a more preferred embodiment the protein kinase substrates comprise or consist of, preferably one or more, phosphorylation sites present in all of the peptide markers listed in Table 1.

A person skilled in the art will appreciate that the phosphorylation sites present in a single peptide marker as listed in Table 1 enable determining the estrogen receptor status of a breast tumor. However, when the number of peptide markers as listed in Table 1 increases, so will increase the specificity and sensitivity of the method according to the present invention. When for example only one protein kinase substrate comprising the phosphorylation sites of a single peptide marker as listed in table 1 is used for determining the estrogen receptor status of a breast tumor the accuracy of the method will be lower, compared to a method where the method uses multiple protein kinase substrates comprising the phosphorylation sites of multiple peptide markers as listed in table 1. The highest method accuracy will be obtained when all protein kinase substrates comprising the phosphorylation sites of all peptide markers as listed in table 1 are used.

TABLE 1 list of 77 peptide markers comprising phosphorylation sites used for determining the kinase activity, their sequence and SEQ ID NO 1 to 77. The name of the peptide markers refers to the associated proteins and also refers to the start and the end position of the amino acid sequence.

| SEQ ID NO | Peptide marker Name | Peptide marker Sequence |
|---|---|---|
| 1 | PGFRB_771_783 | YMAPYDNYVPSAP |
| 2 | VGFR1_1326_1338 | DYNSVVLYSTPPI |
| 3 | PLCG1_764_776 | IGTAEPDYGALYE |
| 4 | PGFRB_709_721 | RPPSAELYSNALP |
| 5 | PDPK1_2_14 | ARTTSQLYDAVPI |
| 6 | DDR1_506_518 | LLLSNPAYRLLLA |
| 7 | EPHA1_774_786 | LDDFDGTYETQGG |
| 8 | FRK_380_392 | KVDNEDIYESRHE |
| 9 | JAK1_1015_1027 | AIETDKEYYTVKD |
| 10 | VGFR2_1168_1180 | AQQDGKDYIVLPI |
| 11 | ADRB2_338_350 | ELLCLRRSSLKAY |
| 12 | PAXI_24_36 | FLSEETPYSYPTG |
| 13 | K2C6B_53_65 | GAGFGSRSLYGLG |
| 14 | MET_1227_1239 | RDMYDKEYYSVHN |
| 15 | NEK2_1_15 | MPSRAEDYEVLYTIG |
| 16 | BCAR1_365_379 | PPPAPDLYDVPPGLR |
| 17 | ANR26_289_303 | RKNLEATYGTVRTGN |
| 18 | HS90B_294_308 | DDITQEEYGEFYKSL |
| 19 | ADAM9_805_819 | PARPAPAPPLYSSLT |
| 20 | A4D108_43_57 | GDVSQFPYVEFTGRD |
| 21 | LDHB_233_247 | KMVVESAYEVIKLKG |
| 22 | EPHB3_607_621 | VYIDPFTYEDPNEAV |
| 23 | Q5VXI6_124_138 | ALEEDVIYDDVPCES |
| 24 | SG269_1100_1114 | PNPCSATYSNLGQSR |
| 25 | ABLM1_350_364 | RTSSESIYSRPGSSI |
| 26 | EFNB1_310_324 | ENNYCPHYEKVSGDY |
| 27 | LPHN2_1399_1413 | RSENEDIYYKSMPNL |
| 28 | STAM2_364_378 | LVNEAPVYSVYSKLH |
| 29 | TENS3_347_361 | GPVDGSLYAKVRKKS |
| 30 | KIRR1_714_728 | SGLERTPYEAYDPIG |

TABLE 1-continued list of 77 peptide markers comprising phosphorylation sites used for determining the kinase activity, their sequence and SEQ ID NO 1 to 77. The name of the peptide markers refers to the associated proteins and also refers to the start and the end position of the amino acid sequence.

| SEQ ID NO | Peptide marker Name | Peptide marker Sequence |
|---|---|---|
| 31 | LMO7_341_355 | RSWASPVYTEADGTF |
| 32 | ZO2_1111_1125 | AQKHPDIYAVPIKTH |
| 33 | MEMO1_203_217 | DESQGEIYRSIEHLD |
| 34 | ABLM1_454_468 | GSINSPVYSRHSYTP |
| 35 | LYN_498_512 | DDFYTATEGQYQQQP |
| 36 | EPHB2_773_787 | DDTSDPTYTSALGGK |
| 37 | DDX3X_259_273 | RYGRRKQYPISLVLA |
| 38 | ERBB2_870_882 | LDIDETEYHADGG |
| 39 | MK10_214_226 | AGTSFMMTPYVVT |
| 40 | ANXA2_17_29 | HSTPPSAYGSVKA |
| 41 | SYVC_871_885 | IDPLDVIYGISLQGL |
| 42 | ANXA1_14_26 | IENEEQEYVQTVK |
| 43 | FGFR2_762_774 | TLTTNEEYLDLSQ |
| 44 | 41_653_665 | RLDGENIYIRHSN |
| 45 | RET_1022_1034 | TPSDSLIYDDGLS |
| 46 | ERBB2_1241_1253 | PTAENPEYLGLDV |
| 47 | EPHA7_607_619 | TYIDPETYEDPNR |
| 48 | P85A_600_612 | NENTEDQYSLVED |
| 49 | PDPK1_369_381 | DEDCYGNYDNLLS |
| 50 | EFS_246_258 | GGTDEGIYDVPLL |
| 51 | ELMO2_706_720 | IPKEPSSYDFVYHYG |
| 52 | Q86W07_1330_1344 | QVFYNSEYGELSEPS |
| 53 | P85B_598_612 | KNETEDQYALMEDED |
| 54 | FGD6_747_761 | EYENIRHYEEIPEYE |
| 55 | SNX3_15_29 | PQNLNDAYGPPSNFL |
| 56 | SNAG_298_312 | TAADEEEDEYSGGLC |
| 57 | IRS2_816_830 | CGGDSDQYVLMSSPV |
| 58 | ITSN2_960_974 | REEPEALYAAVNKKP |
| 59 | ADDB_482_496 | PNQFVPLYTDPQEVL |
| 60 | UB713_323_337 | CPFIDNTYSCSGKLL |
| 61 | CK059_33_47 | LNGAEPNYHSLPSAR |
| 62 | MAP1B_1882_1896 | PDEEDYDYESYEKTT |
| 63 | MALD2_7_21 | SRNRDRRYDEVPSDL |
| 64 | TRXR1_295_309 | NKGKEKIYSAERFLI |
| 65 | ACTG_159_173 | VTHTVPIYEGYALPH |
| 66 | SNIP_129_143 | IYRKEPLYAAFPGSH |
| 67 | CBL_667_681 | SSSANAIYSLAARPL |
| 68 | ZNRF3_401_415 | RHGEQSLYSPQTPAY |
| 69 | BCAR1_320_334 | PLLREETYDVPPAFA |
| 70 | INT7_928_942 | VKSLEDPYSQQIRLQ |
| 71 | FAK1_854_868 | PIGNQHIYQPVGKPD |
| 72 | DOK1_402_416 | YNPATDDYAVPPPRS |
| 73 | CALR3_68_82 | TTQNGRFYAISARFK |
| 74 | HNRPF_299_313 | KATENDIYNFFSPLN |
| 75 | PABP1_357_371 | IVATKPLYVALAQRK |
| 76 | TWF1_320_334 | ELTADFLYEEVHPKQ |
| 77 | SPAST_205_219 | SKSQTDVYNDSTNLA |

It should further be noted that according to a preferred embodiment of the present invention the peptide markers as listed in Table 1 can be used as such for carrying out the methods according to the present invention. The present invention however also includes the use of analogs and combinations of these peptide markers for use in the method according to the present invention. The peptide marker analogs include peptide markers which show a sequence identity of more than 70%, preferably more than 80% and more preferably more than 90%.

In yet another embodiment, the present invention relates to a method according to the present invention wherein step (b) is replaced by steps (c) and (d) as provided below. The method according to the present invention may therefore comprise the steps of:

(a) measuring the kinase activity of a sample from said breast tumor, thereby providing a phosphorylation profile of said sample;

(c) calculating a classifier parameter from said phosphorylation profile; and, (d) determining the estrogen receptor status of said breast tumor on the basis of said classifier parameter.

By establishing a classifier parameter for determining the estrogen receptor status of a breast tumor the method of the present invention provides a criterion for analysing the results obtained from the method of the present invention. This criterion enables a person to provide a diagnosis or prognosis on the basis of a single or limited number of data. The person providing the diagnosis or prognosis does not have to interpret an entire set of data, but rather bases his conclusion on the basis of a single or limited number of criteria.

The term "classifier parameter" as used herein is a discriminating value which has been determined by establishing the phosphorylation profile of said sample. Said discriminating value determines the estrogen receptor status of said breast tumor. The classifier parameter includes information regarding the phosphorylation level of several protein kinase substrates.

Classification is a procedure in which individual items are placed into groups based on quantitative information on one or more characteristics inherent in the items (e.g. phosphorylation levels or profiles of a sample) and based on a training set of previously labelled items (estrogen receptor positive or estrogen receptor negative). A classifying parameter is calculated by applying a "classifier" to the measured phosphorylation levels of a sample. Based on the classifying parameter a sample is assigned to (or predicted to belong to) a class (estrogen receptor positive or estrogen receptor negative) or in another embodiment of the present invention as being responsive or non-responsive to one or more protein kinase inhibitors. The classifier has been previously determined by comparing samples which are known to belong to the respective relevant classes. For instance the classifier may be a mathematical function that uses information regarding the phosphorylation level of several protein kinase substrates which individual protein kinase substrates can be weighted based on the measured phosphorylation level of a number of protein kinase substrates (or values derived from that). Several methods are known in the art for developing a classifier including the neural network (Multi-layer Perceptron), support vector machines, k-nearest neighbors, Gaussian mixture model, naive bayes, decision tree, RBF classifiers, random forest, disciminant analysis, linear discriminant analysis, quadratic discriminant analysis, discriminant analysis—principal component analysis, partial least squares discriminant analysis, generalized distance regression and elastic net classification.

It is not relevant to give an exact threshold value for the classifier parameter. A relevant threshold value can be obtained by correlating the sensitivity and specificity and the sensitivity/specificity for any threshold value. A threshold value resulting in a high sensitivity results in a lower specificity and vice versa. If one wants to increase the positive predictive value of the test to predict whether a breast tumor is estrogen receptor positive then the threshold value of the test can be changed which as a consequence will decrease the negative predictive value of the test to predict estrogen receptor negative patients. If one wants to increase the negative predictive value of the test to predict whether a breast tumor is estrogen receptor negative then the threshold value can be changed in the opposite direction which as a consequence will decrease the positive predictive value of the test to predict breast cancer estrogen receptor positive patients.

It is thus up to the individual diagnostic engineers to determine which level of positive predictive value/negative predictive value/sensitivity/specificity is desirable and how much loss in positive or negative predictive value is tolerable. The chosen threshold level could be dependent on other diagnostic parameters used in combination with the present method by the individual diagnostic engineers.

In yet another embodiment, the present invention relates to a method according to the present invention wherein said classifier parameter indicates an estrogen receptor positive breast tumor if said classifier parameter is above a first predetermined threshold level, and wherein said classifier parameter indicates an estrogen receptor negative breast tumor if said classifier parameter is below a second predetermined threshold level.

In yet another embodiment, the present invention relates to a method according to the present invention wherein step (b) is replaced by steps (e) and (f) as provided below. The method according to the present invention may therefore comprise the steps of:

(a) measuring the kinase activity of a sample from said breast tumor, thereby providing a phosphorylation profile of said sample;

(e) comparing said phosphorylation profile to a first and a second reference phosphorylation profile; said first reference phosphorylation profile being representative for an estrogen receptor positive tumor and said second reference phosphorylation profile being representative for an estrogen receptor negative tumor; and, (f) determining the estrogen receptor status of said breast tumor on the basis of the comparison of said phosphorylation profile with said first and said second reference phosphorylation profile.

As used herein, a "reference phosphorylation profile" refers to a profile obtained through measuring the phosphorylation levels of protein kinase substrates. More specifically, an estrogen receptor positive reference phosphorylation profile as used herein, refers to a reference phosphorylation profile wherein the phosphorylation levels of a set of protein kinase substrates are representative for an estrogen receptor positive breast tumor. Additionally, an estrogen receptor negative reference phosphorylation profile as used herein, refers to a reference phosphorylation profile wherein the phosphorylation levels of a set of protein kinase substrates are representative for an estrogen receptor negative breast tumor.

The tissue-specific template can further be defined as the error-weighted log ratio average of the phosphorylation difference for the group of protein kinase substrates able to determine the estrogen receptor status of a breast tumor.

According to another embodiment, the present invention relates to the method of the present invention wherein said breast tumor is indicated as an estrogen receptor positive breast tumor, an estrogen receptor negative breast tumor or an estrogen receptor undetermined or intermediate breast tumor.

As used in the present application the estrogen receptor status of a breast tumor is generally divided into two types, estrogen receptor positive or estrogen receptor negative and additionally some the estrogen receptor status of same breast tumors may be undetermined or intermediate. Whereas early and advanced estrogen receptor positive breast tumor can preferably be treated with either aromatase inhibitors or anti-estrogen therapy, estrogen receptor negative breast tumors are treated with Herceptin in case of HER2 positive early or advanced tumors or with chemotherapy in case of triple negative tumors. The determination of the estrogen receptor status would also allow to choose other known therapies suited for said breast tumor. The method of the present invention specifically enables the distinction between estrogen receptor positive and estrogen receptor negative breast tumors. The identification of the estrogen receptor status also provides information regarding the best suited treatment of the patient.

In another embodiment, the present invention regards the method according to the present invention wherein said peptide markers are any of the peptide markers selected from the group consisting of the peptide markers with any of SEQ ID NO 1 to 37.

More particularly said protein kinase substrates represent the, preferably one or more, phosphorylation sites present in at least 2, 3, 4, 5, 6, 7, 8, 9, 10, 11, 12, 13, 14, 15, 16, 17, 18, 19, 20, 21, 22, 23, 24, 25, 26, 27, 28, 29, 31, 32, 33, 34, 35, 36 or 37 peptide markers with any of SEQ ID NO 1 to 37. In a more preferred embodiment the protein kinase substrates comprise or consist of, preferably one or more, phosphorylation sites present in all of the peptide markers with any of SEQ ID NO 1 to 37.

In another embodiment, the present invention regards the method according to the present invention wherein said peptide markers are any of the peptide markers selected from the group consisting of the peptide markers with any of SEQ ID NO 3 to 77.

More particularly said protein kinase substrates represent the, preferably one or more, phosphorylation sites present in at least 2, 3, 4, 5, 6, 7, 8, 9 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, or 75 peptide markers with any of SEQ ID NO 3 to 77. In a more preferred embodiment the protein kinase substrates comprise or consist of, preferably one or more, phosphorylation sites present in all of the peptide markers with any of SEQ ID NO 3 to 77.

In another embodiment, the present invention regards the method according to the present invention wherein said peptide markers are any of the peptide markers selected from the group consisting of the peptide markers with any of SEQ ID NO 1 to 15.

More particularly said protein kinase substrates represent the, preferably one or more, phosphorylation sites present in at least 2, 3, 4, 5, 6, 7, 8, 9, 10, 11, 12, 13, 14 or 15 peptide markers with any of SEQ ID NO 1 to 15. In a more preferred embodiment the protein kinase substrates comprise or consist of, preferably one or more, phosphorylation sites present in all of the peptide markers with any of SEQ ID NO 1 to 15.

In another embodiment, the present invention regards the method according to the present invention wherein said peptide markers are any of the peptide markers selected from the group consisting of the peptide markers with any of SEQ ID NO 3 to 15 and 38 to 50.

More particularly said protein kinase substrates represent the, preferably one or more, phosphorylation sites present in at least 2, 3, 4, 5, 6, 7, 8, 9 10, 11, 12, 13, 14, 15, 16, 17, 18, 19, 20, 21, 22, 23, 24, 25 or 26 peptide markers with any of SEQ ID NO 3 to 15 and 38 to 50. In a more preferred embodiment the protein kinase substrates comprise or consist of, preferably one or more, phosphorylation sites present in all of the peptide markers with any of SEQ ID NO 3 to 15 and 38 to 50.

As used herein, the term "protein kinase inhibitor" refers to a type of enzyme inhibitor which blocks the action of one or more protein kinases, hence they can be subdivided or characterised by peptides or proteins whose phosphorylation is inhibited. Examples of protein kinase inhibitors for use in the method of the present invention are dasatinib (currently used for the treatment of leukaemia); erlotinib (currently used for the treatment of non-small cell lung cancer); gefitinib (currently used for the treatment of non-small cell lung cancer); imatinib (currently used for the treatment of gastrointestinal stromal tumors and leukaemia); lapatinib (currently used for the treatment of breast cancer); nilotinib (currently used for the treatment of leukaemia); sorafinib (currently used for the treatment of renal cell carcinoma and hepatocellular carcinoma; Sunitinib (currently used for the treatment of renal cell carcinoma); temsirolimus (currently used for the treatment of renal cell carcinoma); ABT-869; AEE788; Alvocidib; AP23464; AP23846; AP23848; ARRY-142886; ARRY-334543; AT-7519; Axitinib; AZD0530; AZD1152; BIBW-2992; BIRB-796; BMI-1026; BMS-599626; Bosutinib; Brivanib; Canertinib; CCT129202; Cediranib; CEP-7055; CP-547632; CP-724714; Dovitinib; E7080; Enzastaurin; everolimus; FI-700; Gossypol; HKI-272; HMN-176; HMN-214; INNO-406; JNJ-7706621; KRX-0601; LBW242; Lestaurtinib; Midostaurin; MK-0457; MLN8054; MP-470; Neratinib; ON0123380; ON01910; ON-01910; OSI-930; Pazopanib; PD166326; PD173955; PD180970; Pelitinib; PF-2341066; PHA665752; PHA-739358; PX-866; R-547; Seliciclib; Semapimod; Semaxanib; SNS-032; SU011248; SU014813; SU11248; SU11274; SU14813; Tandutinib; Telatinib; TSU-68; UCN-01; Vandetanib; Vatalanib; VE-465; ZM 447439 and protein kinase inhibitors used in research including Tyrphostin-1; Tyrphostin-23; Tyrphostin-51; Tyrphostin-63; AG-1007; AG-1112; AG-1433; RG-13022; SU-1498; I-OMe-Tyrphostin; AG-538; Protein Kinase G inhibitor peptide (Arg-Lys-Arg-Ala-Arg-Lys-Glu); Geldanamycin from *Streptomyces hygroscopicus*; Lavendustin A; and Genistein. More preferably for the purpose of the present invention, said protein kinase inhibitors are protein kinase inhibitors chosen from the group comprising erlotinib, gefitinib, lapatinib, sorafenib and/or sunitinib.

Additionally, the inventors have further found that by adding a protein kinase inhibitor in step (a) of the method of the present invention allows further differentiation between the obtained phosphorylation profiles. When using both a protein kinase inhibitor while measuring the kinase activity, two different phosphorylation profiles can be obtained: a phosphorylation profile in the absence of a protein kinase inhibitor and a phosphorylation profile in the presence of a protein kinase inhibitor. By providing two different phosphorylation profiles more information regarding the estrogen receptor status can be obtained. Another embodiment of the present invention relates to a method according to the present invention wherein said kinase substrates carrying phosphorylation sites are located or immobilized on a solid support, and preferably a porous solid support. Preferably said immobilized kinase substrates carrying phosphorylation sites will be immobilized proteins, peptides or peptide mimetics.

In a preferred embodiment of the present invention peptides are immobilized on a solid support.

As used herein "peptide" refers to a short truncated protein generally consisting of 2 to 100, preferably 2 to 30, more preferably 5 to 30 and even more preferably 13 to 18 naturally occurring or synthetic amino acids which can also be further modified including covalently linking the peptide bonds of the alpha carboxyl group of a first amino acid and the alpha amino group of a second amino acid by eliminating a molecule of water. The amino acids can be either those naturally occurring amino acids or chemically synthesized variants of such amino acids or modified forms of these amino acids which can be altered from their basic chemical structure by addition of other chemical groups which can be found to be covalently attached to them in naturally occurring compounds.

As used herein "protein" refers to a polypeptide made of amino acids arranged in a linear chain and joined together by peptide bonds between the carboxyl and amino groups of adjacent amino acid residues.

As used herein "peptide mimetics" refers to organic compounds which are structurally similar to peptides and similar to the peptide sequences list in Table 1. The peptide mimetics are typically designed from existing peptides to alter the molecules characteristics. Improved characteristics can involve, for example improved stability such as resistance to enzymatic degradation, or enhanced biological activity, improved affinity by restricted preferred conformations and ease of synthesis. Structural modifications in the peptidomimetic in comparison to a peptide, can involve backbone modifications as well as side chain modification.

For measuring the kinase activity of the sample a large variety of methods and formats are known in the art. The kinase activity can for example be measured using ELISA and multiplex ELISA techniques, blotting methods, mass spectrometry, capillary electrophoresis, bead arrays, macroarrays, microarrays or any other method known in the art. Depending on the type of kinase activity measurement method the solid support on which the proteins, peptides or peptide mimetics are fixed may vary. Whereas in ELISA the protein kinase substrates are attached to the surface of the microtiterplates, in microarrays the protein kinase substrates are immobilized on and/or in the microarray substrate.

In a preferred embodiment of the present invention the protein kinase substrates are immobilized on an array, and preferably a microarray of protein kinase substrates wherein the protein kinase substrates are immobilized onto a solid support or another carrier. The immobilization can be either the attachment or adherence of two or more protein kinase substrate molecules to the surface of the carrier including attachment or adherence to the inner surface of said carrier in the case of e.g. a porous or flow-through solid support.

In a preferred embodiment of the present invention, the array of protein kinase substrates is a flow-through array. The flow-through array as used herein could be made of any carrier material having oriented through-going channels as are generally known in the art, such as for example described in PCT patent publication WO 01/19517. Typically the carrier is made from a metal oxide, glass, silicon oxide or cellulose. In a particular embodiment the carrier material is made of a metal oxide selected from the group consisting of zinc oxide, zirconium oxide, tin oxide, aluminium oxide, titanium oxide and thallium; in a more particular embodiment the metal oxide consists of aluminium oxide.

Accordingly, in a further embodiment of the present invention said array is a Pamchip®.

In a further embodiment, the present invention relates to a method according to the present invention wherein said solid support (microarray) comprises any of the peptides as listed in Table 1 immobilized thereto.

In a further embodiment, the present invention relates to a method according to the present invention wherein said solid support (microarray) comprises each of the peptide as listed in Table 1 immobilized thereto.

Another embodiment of the present invention regards a method for predicting the response of a patient, diagnosed with breast cancer, to a medicament, wherein the kinase activity of a sample, obtained from the breast tumor, is measured in the presence and in the absence of said medicament and wherein said kinase activity in the presence of said medicament is compared to the kinase activity in the absence of said medicament thereby determining the response of said patient to said medicament, wherein said kinase activity measurement provides phosphorylation profiles of said sample in the presence and in the absence of said medicament.

By measuring the kinase activity of a sample, obtained from the breast tumor from said patient, in the presence and in the absence of a medicament, the effect of that medicament to the breast tumor can be assessed. This method was found particularly useful in the prediction of response to said medicament, and to enable the distinction between responders and non-responders in the treatment with said medicament. The measurement of the kinase activity of said sample preferably occurs by contacting said sample with at least one protein kinase substrate in the presence and in the absence of said medicament. Techniques from the prior art often require the incubation of the cells or tissues with said medicaments preferably in vivo, during the culturing of the cells or tissues or during a large time period prior to the actual measurement of the kinase activity. The present invention provides that the medicament is added directly to the sample and preferably directly to the lysate sample. The medicament is added to the sample only just prior to contacting the sample with the protein kinase substrates and performing the kinase activity assay. Consequently, the medicament is added in vitro at the time the incubation of the lysate sample with the protein kinase substrates is initiated. The present invention therefore provides an in vitro primary screening tool which allows the use of a single sample which is split into a first part that is used for the incubation of the sample in the absence of a medicament while a second part of the sample is used for the incubation of the sample in the presence of a medicament.

It should be noted that the observed response of the patient to said medicament can either be a positive response, wherein the medicament will improve the treatment of said patient, or a negative response, wherein the medicament has a negative or no influence on the treatment of said patient.

The medicament as used in the method of the present invention can be any kind of chemical substance for instance used in the treatment, cure, prevention, or diagnosis of disease or used to otherwise enhance physical or mental well-being. Specifically said medicament can be a kinase inhibitor, and more preferably a protein kinase inhibitor and most preferably a small molecule protein kinase inhibitor.

In another embodiment of the present invention the method for determining the estrogen receptor status of a breast tumor to a medicament, uses phosphorylation profiles which comprise the phosphorylation levels of, preferably one or more, phosphorylation sites present in any of the peptide markers as listed in Table 1.

Preferably also this method will use two or more of said peptide markers as described above. More preferably this method will use, preferably one or more, phosphorylation sites present in at least 2, 3, 4, 5, 6, 7, 8, 9 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, or 77 of the peptide markers listed in Table 1.

Also for this embodiment, the amount and the type of peptides, proteins or peptide mimetics to be used is as described above. Phosphorylation levels can also be measured according to the invention, without the necessity to generate phosphorylation profiles thereof.

It is clear that effects of a medicament can be monitored using this method. The medicament affects the degree of inhibition, the potency and/or the selectivity of the kinases in the sample. More peptide inhibition is caused by the larger effect of the medicament on the kinases in the sample and therefore the drug is less selective. Also an increased peptide inhibition would lead to a larger amount of normal tissues being affected by the drug, making the drug less tumor tissue specific.

Another embodiment of the present invention relates to a method for determining the estrogen receptor status of a breast tumor to a medicament, wherein the kinase activity of a sample, obtained from the breast tumor from said patient, is measured in the presence and in the absence of a protein kinase inhibitor targeting a target identical to the target of said medicament and wherein said kinase activity in the presence said protein kinase inhibitor is compared to the kinase activity in the absence of said protein kinase inhibitor thereby determining the response of said patient to said medicament, wherein said kinase activity measurement provides phosphorylation profiles of said sample in the presence and in the absence of said protein kinase inhibitor.

By using a protein kinase inhibitor targeting a target identical to the target of a medicament, the inventors have found that the response of the patient to said medicament can be predicted. This method therefore allows the use of protein kinase inhibitors which have not been clinically approved as agents predicting the response of a patient to a medicament, if said protein kinase inhibitor and said medicament are targeted towards the same target.

The present invention also relates according to another embodiment to an array for carrying out the method of the present invention, said array comprising immobilized proteins, peptides or peptide mimetics comprising, preferably one or more, phosphorylation sites present in any of the peptide markers as listed in table 1. More preferably said array comprises immobilized proteins, peptides or peptide mimetics comprising, preferably one or more, phosphorylation sites present in at least 2, 3, 4, 5, 6, 7, 8, 9 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, or 77 of the peptide markers listed in Table 1.

The present invention also relates according to another embodiment to an array for carrying out the method of the present invention, said array comprising immobilized proteins, peptides or peptide mimetics comprising, preferably one or more, phosphorylation sites present in any of the peptide markers as listed in table 1. More preferably said array comprises immobilized proteins, peptides or peptide mimetics comprising, preferably one or more, phosphorylation sites present in at least 2, 3, 4, 5, 6, 7, 8, 9 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, or 77 of the peptide markers listed in Table 1.

In another embodiment said array comprises immobilized proteins, peptides or peptide mimetics comprising, preferably one or more, phosphorylation sites present in at least 1, 2, 3, 4, 5, 6, 7, 8, 9 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, or 75 peptide markers with any of SEQ ID NO 3 to 77.

In another embodiment said array comprises immobilized proteins, peptides or peptide mimetics comprising, preferably one or more, phosphorylation sites present in at least 1, 2, 3, 4, 5, 6, 7, 8, 9, 10, 11, 12, 13, 14 or 15 peptide markers with any of SEQ ID NO 1 to 15.

In another embodiment said array comprises immobilized proteins, peptides or peptide mimetics comprising, preferably one or more, phosphorylation sites present in at least 1, 2, 3, 4, 5, 6, 7, 8, 9 10, 11, 12, 13, 14, 15, 16, 17, 18, 19, 20, 21, 22, 23, 24, 25 or 26 peptide markers with any of SEQ ID NO 3 to 15 and 38 to 50.

Said proteins, peptides or peptide mimetics are preferably at least 25% of proteins, peptides or peptide mimetics on said array. Said arrays may further comprise one or more immobilized proteins, peptides or peptide mimetics which are used as calibration means for performing the methods according to the present invention.

More particularly said array comprises immobilized proteins, peptides or peptide mimetics comprising, preferably one or more, phosphorylation sites as described in detail above representing the peptide markers as listed in table 1.

Additionally said proteins, peptides or peptide mimetics are preferably at least 25%, at least 50%, at least 70%, at least 80%, at least 90% or 100% of the proteins, peptides or peptide mimetics on said array.

The type of arrays to be used according to this embodiment are known in the art and are further detailed above.

The present invention also relates in another embodiment to a computer program product for use in conjunction with a computer having a processor and a memory connected to the processor, said computer program product comprising a computer readable storage medium having a computer program mechanism encoded thereon, wherein said computer program mechanism may be loaded into the memory of said computer and cause said computer to carry out the method according to the present invention.

The present invention further relates to a computer system comprising a processor, and a memory coupled to said processor and encoding one or more programs, wherein said one or more programs instruct the processor to carry out the methods according to the present invention.

The present invention also relates in another embodiment to a kit for determining the estrogen receptor status of a breast tumor, comprising at least one array according to the present invention, and optionally a computer readable medium having recorded thereon one or more programs for carrying out the method according to the present invention.

The present invention further relates in yet another embodiment to a method for determining the estrogen receptor status of a breast tumor, comprising the steps of:

(a) measuring the kinase activity of a sample, obtained from the breast tumor, in the presence and in the absence of a protein kinase inhibitor, thereby providing a phosphorylation profile of said sample; and, (b) determining from said phosphorylation profile the estrogen receptor status of said breast tumor.

Since the present inventors have identified a surprisingly useful set of peptide markers to be used in methods for determining the estrogen receptor status of a breast tumor, the skilled person may carry out any method as defined above wherein he measures the kinase activity of any of the peptide markers of Table 1. Also this method may be carried out using the amount and type of peptides, proteins or protein mimetics as defined above. The formats for carrying out these methods are also as for the methods described above.

The present invention is hereafter exemplified by the illustration of particular, non-limiting examples.

EXAMPLES

Example 1

Example Determining the Diagnostic Set of 77 Peptide Markers

The method of the present invention allows the measurement of the kinase activity in lysates prepared from fresh frozen breast cancer tumors. 23 frozen breast cancer tumors were analysed according to the method of the present invention. The ER status of the tumors was first determined using a conventional method known in the art. 12 patients had a positive ER status, 11 patients a negative ER status. The ER status of each breast cancer tumor sample was measured 3 times.

6 coupes of 10 µm thickness of tumor tissue were lysed in 100 microliter Mammalian Protein Extraction Buffer (M-PER) containing phosphatase and protease inhibitors. After 30 minutes of lysis on ice, and centrifugation for 15 min at 4° C., the supernatants were aliquotted and frozen. 10 microgram protein contained in the lysis solution was pipetted into a reaction mixture composed of 1× ABL buffer (10× Abl buffer New England Biolabs, cat.nr B6050S-100 mM MgCl2, 10 mM EGTA, 20 mM DTT and 0.1% Brij 35 in 500 mM Tris/HCl, pH 7.5), 0.1% Bovine Serum Albumin, 100 μM ATP, 12.5 μg/ml phosphotyrosine antibody to an end volume of 40 microliter. The substrate arrays were blocked with 2% BSA just before the start of the incubation, followed by 3× washing of the arrays with 1×Abl buffer. After loading of the lysate reaction mixtures into substrate arrays comprising 256 protein kinase substrates, including the 77 protein kinase peptide substrates as listed in Table 1, incubation was commenced thereby measuring the kinase activity of the sample. During 60 cycles of pumping the lysate reaction mixture through the array, peptide phosphorylation was detected by an antibody present in the lysate reaction mixture. Real time data were obtained by measuring fluorescence of the bound anti-phosphotyrosine antibody after each 5 cycles. Images of the array were taken during the incubation of the array and after 60 cycles of incubation. After 60 cycles of incubation and imaging, the antibody mixture was removed and the array was washed. Images were collected at different exposure times.

Signals for each spot on the image were quantified. Image quantification and data processing was conducted with dedicated PamGene software (Evolve and Bionavigator).

Subsequent data analysis was performed using Matlab (release 2007B, MathWorks Inc.) wherein the phosphorylation signals were normalized, the average of the signal per spot was calculated and unsupervised analysis was performed by applying principal component analysis (PCA) to the obtained data.

FIG. 1 shows the scores on the 4th principal component (PC) on the X-axis and that of the fifth PC on the Y axis. Each point represents one of the 23 samples, filled circles represent ER negative samples and open circles represent ER positive samples. It can be seen that clusters for ER positive samples and ER negative samples can be determined. This is a strong indication that ER positive and ER negative samples can indeed be discriminated between.

Figure 2:
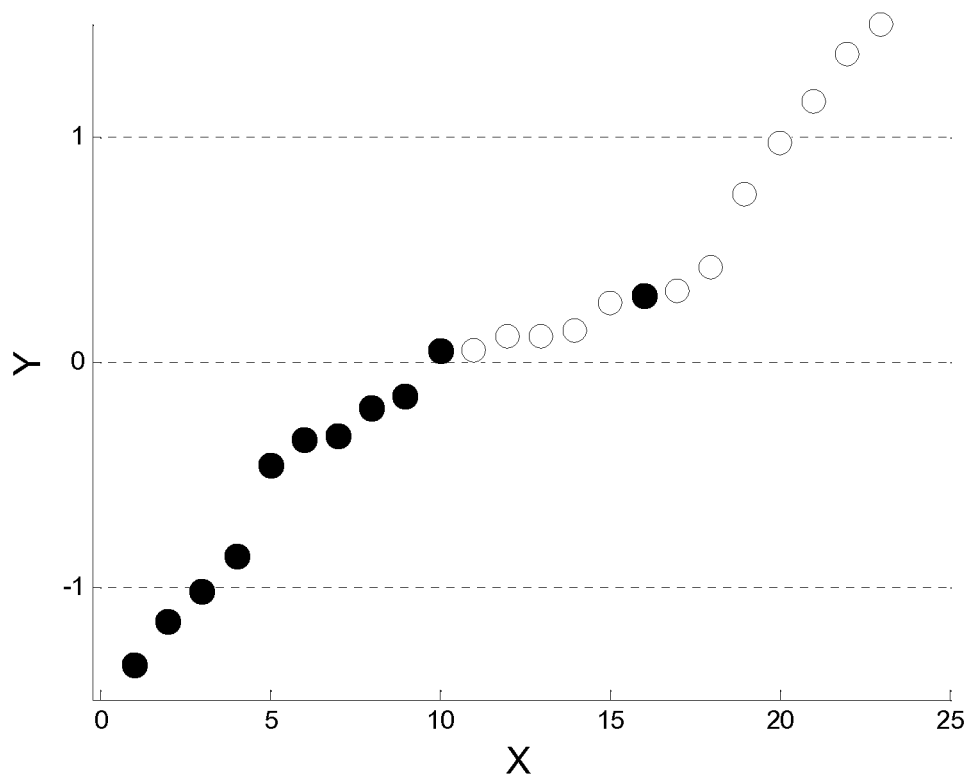
FIG. 2 provides, as depicted in the examples, a graphical representation of the sorting of breast tumor samples according to the ER status, wherein the Y-axis provides the prediction for each sample wherein ER negative samples are represented by a filled symbol, ER positive samples by an open symbol.

A classifier for ER-positive and ER-negative samples based on all the 256 spots in measurements could be constructed by applying Partial Least Squares Discriminant Analysis (PLS-DA). The performance of the classifier in predicting the class of an unseen sample was evaluated by applying Leave One Out Cross Validation: the classification of each individual breast tumor sample (the "test sample") was predicted by a classifier based on all other samples (the "training samples"). The test sample was not involved in any way in constructing or optimizing the classifier, for each iteration of the cross validation the optimal number of PLS components was determined based on the training samples only. This procedure resulted in an unbiased estimate of the prediction error of the classifier. In total 75 protein kinase substrates were used in the PLS classifier (SEQ ID NO 3 to 77) and used to predict the ER status of each of the samples as shown in FIG. 2. In a separate embodiment of the invention the PLS classifier contains the protein kinase substrates with SEQ ID NO. 3 to 15 and 38 to 50.

For each of the protein kinase substrates a univariate Anova was performed using the Matlab Statistics Toolbox 7.1. This protein kinase substrate profile is based on the protein kinase substrates with SEQ ID NO 1 to 37 which have a p-value of <0.05 in the Anova. In a separate embodiment of the invention the Anova selected contain the protein kinase substrates with SEQ ID NO 1 to 15.

FIG. 2 shows on the Y-axis the prediction obtained for each sample. The samples are sorted along the X-axis. ER negative samples are represented by a filled symbol, ER positive samples by an open symbol. Samples are classified as ER negative if the prediction <0 and as ER positive if the prediction >0. It can be seen that 2 ER negative samples are erroneously classified as ER positive samples: the classification error is 8.7%.

Consequently, the present example shows that the method of the present invention provides a set of peptide markers that enable the prediction of the ER status of a breast cancer, and moreover enables the classification of breast cancer according to the ER status.

Example 2

Example Determining the Diagnostic Set of 20 Peptide Markers

In a separate study the study in Experiment 1 was repeated. The data from both experiments were analysed and the performance of the PLS-DA classification method was estimated using a leave-one-out-cross-validation. The classification prediction error using up to 190 protein kinase substrates on the arrays was 15%. Secondly the prediction error of the classification method was tested by testing the prediction error by excluding N most significant peptides from a univariate test. A univariate test was based on a t-test on equal signal in the ER positive and ER negative condition after the centering correction.

Figure 3:
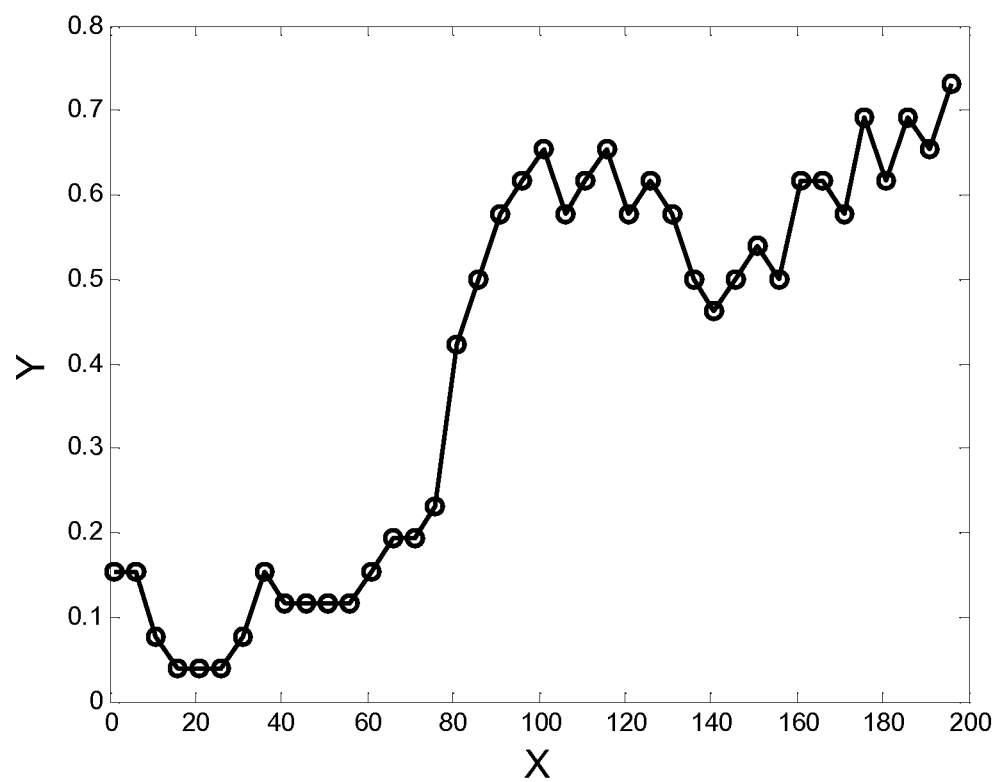
FIG. 3 provides, as depicted in the examples, a graphical representation regarding the influence of the number of peptide markers for determining the estrogen receptor status of a breast tumor on the accuracy of the method of the present invention.

FIG. 3 shows on the X-axis the number of protein kinase substrates excluded, in steps of 5, from the classification starting the protein kinase substrates with the highest p-value in the Anova. The Y-axis describes the prediction error of the classification showing a steep rise in the classification method when removing more than 75 protein kinase substrates from the classification method. This prediction error or classification error increases to values >30% when more than 75 most significant protein kinase substrates are excluded from the model. This shows that the most significant protein kinase peptides are the protein kinase substrates in Table 1 with SEQ ID NO 3 to 77.

The invention claimed is:

1. A method for determining the estrogen receptor status of a breast tumor said estrogen receptor status indicating whether said breast tumor is estrogen receptor positive, estrogen receptor negative, or undetermined, comprising the steps of:
   (a) measuring kinase activity of a sample from said breast tumor by:
      (i) contacting said sample with a plurality of solid support-immobilized protein kinase substrates comprising the peptide markers having SEQ ID NO: 3 to 15 and 38 to 50, and
      (ii) measuring phosphorylation among the plurality of immobilized protein kinase substrates, thereby providing a phosphorylation profile of said sample, wherein the phosphorylation profile of the sample is indicative of the phosphorylation profile of the tumor; and,
   (b) determining from the sample's phosphorylation profile of step (a) the estrogen receptor status of said breast tumor.

2. The method according to claim 1, wherein in step (b) the determining of the estrogen receptor status of from the sample phosphorylation profile comprises the steps of:
   (i) calculating a classifier parameter from the sample phosphorylation profile followed by
   (ii) determining from the classifier parameter the estrogen receptor status of said breast tumor,
   wherein said classifier parameter indicates an estrogen receptor positive breast tumor if said classifier parameter is above a first predetermined threshold level, and wherein said classifier parameter indicates an estrogen receptor negative breast tumor if said classifier parameter is below a second predetermined threshold level.

3. The method according to claim 1, wherein the determining of the estrogen receptor status of step (b) comprises the steps of:
   (i) comparing said sample phosphorylation profile to:
      (a') a first phosphorylation profile which is representative of an estrogen receptor positive breast tumor and
      (b') a second reference phosphorylation profile which is representative of an estrogen receptor negative breast tumor, followed by
   (ii) determining from the comparing of step (b)(i), the estrogen receptor status of said breast tumor.

4. The method according to claim 1, wherein said breast tumor is indicated as an estrogen receptor positive breast tumor, an estrogen receptor negative breast tumor or an estrogen receptor undetermined breast tumor.

5. The method according to claim 1, wherein the solid support is a porous solid support.

6. The method for determining the estrogen receptor status of a breast tumor of claim 1, wherein in step (a) (ii) the phosphorylation profile of the sample is the profile of the phosphorylation levels of the plurality of immobilized protein kinase substrates.

7. The method according to claim 6, wherein the solid support is a porous solid support.

8. A method for determining the response of a patient diagnosed with breast cancer to a medicament, comprising:
  (a) measuring kinase activity of a sample from said breast cancer in the presence and in the absence of said medicament by:
    (i) contacting in the presence of and in the absence of said medicament said sample with a plurality of solid support-immobilized protein kinase substrates comprising the peptide markers having SEQ ID NO: 3 to 15 and 38 to 50, and
    (ii) measuring phosphorylation among the plurality of immobilized protein kinase substrates, thereby providing a phosphorylation profile of said sample in the presence of and in the absence of said medicament, wherein the phosphorylation profile of the sample is indicative of the phosphorylation profile of the breast cancer; and,
  (b) determining from the sample's phosphorylation profile of step (a) the kinase activity response of said breast cancer to said medicament, wherein the kinase activity response is indicative of the of patient kinase activity response to said medicament.

9. An array for determining the estrogen receptor status of a breast tumor according to the method of claim 1, said array having immobilized thereupon a plurality of immobilized protein kinase substrates, wherein the plurality of kinase substrates comprises the peptide markers having SEQ ID NO: 3 to 15 and 38 to 50.

10. A kit for determining the estrogen receptor status of a breast tumor, comprising at least one array according to claim 9.

11. A kit for determining the estrogen receptor status of a breast tumor, comprising:
  at least one array for determining the estrogen receptor status of a breast tumor according to the method of claim 1, said array having immobilized thereupon a plurality of immobilized protein kinase substrates wherein the plurality of kinase substrates comprises the peptide markers having SEQ ID NO: 3 to 15 and 38 to 50; and
  a computer readable storage medium having recorded thereon one or more programs for carrying out the method of claim 1.

* * * * *

SEQUENCE LISTING

<160> NUMBER OF SEQ ID NOS: 77

<210> SEQ ID NO 1
<211> LENGTH: 13
<212> TYPE: PRT
<213> ORGANISM: Artificial Sequence
<220> FEATURE:
<223> OTHER INFORMATION: Peptide PGFRB_771_783

```
<400> SEQUENCE: 1

Tyr Met Ala Pro Tyr Asp Asn Tyr Val Pro Ser Ala Pro
1               5                   10

<210> SEQ ID NO 2
<211> LENGTH: 13
<212> TYPE: PRT
<213> ORGANISM: Artificial Sequence
<220> FEATURE:
<223> OTHER INFORMATION: Peptide VGFR1_1326_1338

<400> SEQUENCE: 2

Asp Tyr Asn Ser Val Val Leu Tyr Ser Thr Pro Pro Ile
1               5                   10

<210> SEQ ID NO 3
<211> LENGTH: 13
<212> TYPE: PRT
<213> ORGANISM: Artificial Sequence
<220> FEATURE:
<223> OTHER INFORMATION: Peptide PLCG1_764_776

<400> SEQUENCE: 3

Ile Gly Thr Ala Glu Pro Asp Tyr Gly Ala Leu Tyr Glu
1               5                   10

<210> SEQ ID NO 4
<211> LENGTH: 13
<212> TYPE: PRT
<213> ORGANISM: Artificial Sequence
<220> FEATURE:
<223> OTHER INFORMATION: Peptide PGFRB_709_721

<400> SEQUENCE: 4

Arg Pro Pro Ser Ala Glu Leu Tyr Ser Asn Ala Leu Pro
1               5                   10

<210> SEQ ID NO 5
<211> LENGTH: 13
<212> TYPE: PRT
<213> ORGANISM: Artificial Sequence
<220> FEATURE:
<223> OTHER INFORMATION: Peptide PDPK1_2_14

<400> SEQUENCE: 5

Ala Arg Thr Thr Ser Gln Leu Tyr Asp Ala Val Pro Ile
1               5                   10

<210> SEQ ID NO 6
<211> LENGTH: 13
<212> TYPE: PRT
<213> ORGANISM: Artificial Sequence
<220> FEATURE:
<223> OTHER INFORMATION: Peptide DDR1_506_518

<400> SEQUENCE: 6

Leu Leu Leu Ser Asn Pro Ala Tyr Arg Leu Leu Leu Ala
1               5                   10

<210> SEQ ID NO 7
<211> LENGTH: 13
<212> TYPE: PRT
<213> ORGANISM: Artificial Sequence
<220> FEATURE:
<223> OTHER INFORMATION: Peptide EPHA1_774_786

<400> SEQUENCE: 7
```

```
Leu Asp Asp Phe Asp Gly Thr Tyr Glu Thr Gln Gly Gly
1               5                   10
```

<210> SEQ ID NO 8
<211> LENGTH: 13
<212> TYPE: PRT
<213> ORGANISM: Artificial Sequence
<220> FEATURE:
<223> OTHER INFORMATION: Peptide frk_380_392

<400> SEQUENCE: 8

```
Lys Val Asp Asn Glu Asp Ile Tyr Glu Ser Arg His Glu
1               5                   10
```

<210> SEQ ID NO 9
<211> LENGTH: 13
<212> TYPE: PRT
<213> ORGANISM: Artificial Sequence
<220> FEATURE:
<223> OTHER INFORMATION: Peptide JAK1_1015_1027

<400> SEQUENCE: 9

```
Ala Ile Glu Thr Asp Lys Glu Tyr Tyr Thr Val Lys Asp
1               5                   10
```

<210> SEQ ID NO 10
<211> LENGTH: 13
<212> TYPE: PRT
<213> ORGANISM: Artificial Sequence
<220> FEATURE:
<223> OTHER INFORMATION: Peptide VGFR2_1168_1180

<400> SEQUENCE: 10

```
Ala Gln Gln Asp Gly Lys Asp Tyr Ile Val Leu Pro Ile
1               5                   10
```

<210> SEQ ID NO 11
<211> LENGTH: 13
<212> TYPE: PRT
<213> ORGANISM: Artificial Sequence
<220> FEATURE:
<223> OTHER INFORMATION: Peptide ADRB2_338_350

<400> SEQUENCE: 11

```
Glu Leu Leu Cys Leu Arg Arg Ser Ser Leu Lys Ala Tyr
1               5                   10
```

<210> SEQ ID NO 12
<211> LENGTH: 13
<212> TYPE: PRT
<213> ORGANISM: Artificial Sequence
<220> FEATURE:
<223> OTHER INFORMATION: Peptide PAXI_24_36

<400> SEQUENCE: 12

```
Phe Leu Ser Glu Glu Thr Pro Tyr Ser Tyr Pro Thr Gly
1               5                   10
```

<210> SEQ ID NO 13
<211> LENGTH: 13
<212> TYPE: PRT
<213> ORGANISM: Artificial Sequence
<220> FEATURE:
<223> OTHER INFORMATION: Peptide K2C6B_53_65

<400> SEQUENCE: 13

```
Gly Ala Gly Phe Gly Ser Arg Ser Leu Tyr Gly Leu Gly
1               5                   10

<210> SEQ ID NO 14
<211> LENGTH: 13
<212> TYPE: PRT
<213> ORGANISM: Artificial Sequence
<220> FEATURE:
<223> OTHER INFORMATION: Peptide MET_1227_1239

<400> SEQUENCE: 14

Arg Asp Met Tyr Asp Lys Glu Tyr Tyr Ser Val His Asn
1               5                   10

<210> SEQ ID NO 15
<211> LENGTH: 15
<212> TYPE: PRT
<213> ORGANISM: Artificial Sequence
<220> FEATURE:
<223> OTHER INFORMATION: Peptide NEK2_1_15

<400> SEQUENCE: 15

Met Pro Ser Arg Ala Glu Asp Tyr Glu Val Leu Tyr Thr Ile Gly
1               5                   10                  15

<210> SEQ ID NO 16
<211> LENGTH: 15
<212> TYPE: PRT
<213> ORGANISM: Artificial Sequence
<220> FEATURE:
<223> OTHER INFORMATION: Peptide BCAR1_365_379

<400> SEQUENCE: 16

Pro Pro Pro Ala Pro Asp Leu Tyr Asp Val Pro Pro Gly Leu Arg
1               5                   10                  15

<210> SEQ ID NO 17
<211> LENGTH: 15
<212> TYPE: PRT
<213> ORGANISM: Artificial Sequence
<220> FEATURE:
<223> OTHER INFORMATION: Peptide ANR26_289_303

<400> SEQUENCE: 17

Arg Lys Asn Leu Glu Ala Thr Tyr Gly Thr Val Arg Thr Gly Asn
1               5                   10                  15

<210> SEQ ID NO 18
<211> LENGTH: 15
<212> TYPE: PRT
<213> ORGANISM: Artificial Sequence
<220> FEATURE:
<223> OTHER INFORMATION: Peptide HS90B_294_308

<400> SEQUENCE: 18

Asp Asp Ile Thr Gln Glu Glu Tyr Gly Glu Phe Tyr Lys Ser Leu
1               5                   10                  15

<210> SEQ ID NO 19
<211> LENGTH: 15
<212> TYPE: PRT
<213> ORGANISM: Artificial Sequence
<220> FEATURE:
<223> OTHER INFORMATION: Peptide ADAM9_805_819

<400> SEQUENCE: 19

Pro Ala Arg Pro Ala Pro Ala Pro Pro Leu Tyr Ser Ser Leu Thr
```

```
1               5                  10                  15

<210> SEQ ID NO 20
<211> LENGTH: 15
<212> TYPE: PRT
<213> ORGANISM: Artificial Sequence
<220> FEATURE:
<223> OTHER INFORMATION: Peptide A4D108_43_57

<400> SEQUENCE: 20

Gly Asp Val Ser Gln Phe Pro Tyr Val Glu Phe Thr Gly Arg Asp
1               5                  10                  15

<210> SEQ ID NO 21
<211> LENGTH: 15
<212> TYPE: PRT
<213> ORGANISM: Artificial Sequence
<220> FEATURE:
<223> OTHER INFORMATION: Peptide LDHB_233_247

<400> SEQUENCE: 21

Lys Met Val Val Glu Ser Ala Tyr Glu Val Ile Lys Leu Lys Gly
1               5                  10                  15

<210> SEQ ID NO 22
<211> LENGTH: 15
<212> TYPE: PRT
<213> ORGANISM: Artificial Sequence
<220> FEATURE:
<223> OTHER INFORMATION: Peptide EPHB3_607_621

<400> SEQUENCE: 22

Val Tyr Ile Asp Pro Phe Thr Tyr Glu Asp Pro Asn Glu Ala Val
1               5                  10                  15

<210> SEQ ID NO 23
<211> LENGTH: 15
<212> TYPE: PRT
<213> ORGANISM: Artificial Sequence
<220> FEATURE:
<223> OTHER INFORMATION: Peptide Q5VX16_124_138

<400> SEQUENCE: 23

Ala Leu Glu Glu Asp Val Ile Tyr Asp Asp Val Pro Cys Glu Ser
1               5                  10                  15

<210> SEQ ID NO 24
<211> LENGTH: 15
<212> TYPE: PRT
<213> ORGANISM: Artificial Sequence
<220> FEATURE:
<223> OTHER INFORMATION: Peptide SG269_1100_1114

<400> SEQUENCE: 24

Pro Asn Pro Cys Ser Ala Thr Tyr Ser Asn Leu Gly Gln Ser Arg
1               5                  10                  15

<210> SEQ ID NO 25
<211> LENGTH: 15
<212> TYPE: PRT
<213> ORGANISM: Artificial Sequence
<220> FEATURE:
<223> OTHER INFORMATION: Peptide ABLM1_350_364

<400> SEQUENCE: 25

Arg Thr Ser Ser Glu Ser Ile Tyr Ser Arg Pro Gly Ser Ser Ile
1               5                  10                  15
```

<210> SEQ ID NO 26
<211> LENGTH: 15
<212> TYPE: PRT
<213> ORGANISM: Artificial Sequence
<220> FEATURE:
<223> OTHER INFORMATION: Peptide EFNB1_310_324

<400> SEQUENCE: 26

Glu Asn Asn Tyr Cys Pro His Tyr Glu Lys Val Ser Gly Asp Tyr
1               5                   10                  15

<210> SEQ ID NO 27
<211> LENGTH: 15
<212> TYPE: PRT
<213> ORGANISM: Artificial Sequence
<220> FEATURE:
<223> OTHER INFORMATION: Peptide LPHN2_1399_1413

<400> SEQUENCE: 27

Arg Ser Glu Asn Glu Asp Ile Tyr Tyr Lys Ser Met Pro Asn Leu
1               5                   10                  15

<210> SEQ ID NO 28
<211> LENGTH: 15
<212> TYPE: PRT
<213> ORGANISM: Artificial Sequence
<220> FEATURE:
<223> OTHER INFORMATION: Peptide STAM2_364_378

<400> SEQUENCE: 28

Leu Val Asn Glu Ala Pro Val Tyr Ser Val Tyr Ser Lys Leu His
1               5                   10                  15

<210> SEQ ID NO 29
<211> LENGTH: 15
<212> TYPE: PRT
<213> ORGANISM: Artificial Sequence
<220> FEATURE:
<223> OTHER INFORMATION: Peptide TENS3_347_361

<400> SEQUENCE: 29

Gly Pro Val Asp Gly Ser Leu Tyr Ala Lys Val Arg Lys Lys Ser
1               5                   10                  15

<210> SEQ ID NO 30
<211> LENGTH: 15
<212> TYPE: PRT
<213> ORGANISM: Artificial Sequence
<220> FEATURE:
<223> OTHER INFORMATION: Peptide KIRR1_714_728

<400> SEQUENCE: 30

Ser Gly Leu Glu Arg Thr Pro Tyr Glu Ala Tyr Asp Pro Ile Gly
1               5                   10                  15

<210> SEQ ID NO 31
<211> LENGTH: 15
<212> TYPE: PRT
<213> ORGANISM: Artificial Sequence
<220> FEATURE:
<223> OTHER INFORMATION: Peptide LMO7_341_355

<400> SEQUENCE: 31

Arg Ser Trp Ala Ser Pro Val Tyr Thr Glu Ala Asp Gly Thr Phe
1               5                   10                  15

```
<210> SEQ ID NO 32
<211> LENGTH: 15
<212> TYPE: PRT
<213> ORGANISM: Artificial Sequence
<220> FEATURE:
<223> OTHER INFORMATION: Peptide ZO2_1111_1125

<400> SEQUENCE: 32

Ala Gln Lys His Pro Asp Ile Tyr Ala Val Pro Ile Lys Thr His
1               5                   10                  15

<210> SEQ ID NO 33
<211> LENGTH: 15
<212> TYPE: PRT
<213> ORGANISM: Artificial Sequence
<220> FEATURE:
<223> OTHER INFORMATION: Peptide MEMO1_203_217

<400> SEQUENCE: 33

Asp Glu Ser Gln Gly Glu Ile Tyr Arg Ser Ile Glu His Leu Asp
1               5                   10                  15

<210> SEQ ID NO 34
<211> LENGTH: 15
<212> TYPE: PRT
<213> ORGANISM: Artificial Sequence
<220> FEATURE:
<223> OTHER INFORMATION: ABLM1_454_468

<400> SEQUENCE: 34

Gly Ser Ile Asn Ser Pro Val Tyr Ser Arg His Ser Tyr Thr Pro
1               5                   10                  15

<210> SEQ ID NO 35
<211> LENGTH: 15
<212> TYPE: PRT
<213> ORGANISM: Artificial Sequence
<220> FEATURE:
<223> OTHER INFORMATION: Peptide LYN_498_512

<400> SEQUENCE: 35

Asp Asp Phe Tyr Thr Ala Thr Glu Gly Gln Tyr Gln Gln Gln Pro
1               5                   10                  15

<210> SEQ ID NO 36
<211> LENGTH: 15
<212> TYPE: PRT
<213> ORGANISM: Artificial Sequence
<220> FEATURE:
<223> OTHER INFORMATION: Peptide EPHB2_773_787

<400> SEQUENCE: 36

Asp Asp Thr Ser Asp Pro Thr Tyr Thr Ser Ala Leu Gly Gly Lys
1               5                   10                  15

<210> SEQ ID NO 37
<211> LENGTH: 15
<212> TYPE: PRT
<213> ORGANISM: Artificial Sequence
<220> FEATURE:
<223> OTHER INFORMATION: Peptide DDX3X_259_273

<400> SEQUENCE: 37

Arg Tyr Gly Arg Arg Lys Gln Tyr Pro Ile Ser Leu Val Leu Ala
1               5                   10                  15
```

-continued

```
<210> SEQ ID NO 38
<211> LENGTH: 13
<212> TYPE: PRT
<213> ORGANISM: Artificial Sequence
<220> FEATURE:
<223> OTHER INFORMATION: Peptide ERBB2_870_882

<400> SEQUENCE: 38

Leu Asp Ile Asp Glu Thr Glu Tyr His Ala Asp Gly Gly
1               5                   10

<210> SEQ ID NO 39
<211> LENGTH: 13
<212> TYPE: PRT
<213> ORGANISM: Artificial Sequence
<220> FEATURE:
<223> OTHER INFORMATION: Peptide MK10_214_226

<400> SEQUENCE: 39

Ala Gly Thr Ser Phe Met Met Thr Pro Tyr Val Val Thr
1               5                   10

<210> SEQ ID NO 40
<211> LENGTH: 13
<212> TYPE: PRT
<213> ORGANISM: Artificial Sequence
<220> FEATURE:
<223> OTHER INFORMATION: Peptide ANXA2_17_29

<400> SEQUENCE: 40

His Ser Thr Pro Pro Ser Ala Tyr Gly Ser Val Lys Ala
1               5                   10

<210> SEQ ID NO 41
<211> LENGTH: 15
<212> TYPE: PRT
<213> ORGANISM: Artificial Sequence
<220> FEATURE:
<223> OTHER INFORMATION: Peptide SYVC_871_885

<400> SEQUENCE: 41

Ile Asp Pro Leu Asp Val Ile Tyr Gly Ile Ser Leu Gln Gly Leu
1               5                   10                  15

<210> SEQ ID NO 42
<211> LENGTH: 13
<212> TYPE: PRT
<213> ORGANISM: Artificial Sequence
<220> FEATURE:
<223> OTHER INFORMATION: Peptide ANXA1_14_26

<400> SEQUENCE: 42

Ile Glu Asn Glu Glu Gln Glu Tyr Val Gln Thr Val Lys
1               5                   10

<210> SEQ ID NO 43
<211> LENGTH: 13
<212> TYPE: PRT
<213> ORGANISM: Artificial Sequence
<220> FEATURE:
<223> OTHER INFORMATION: Peptide FGFR2_762_774

<400> SEQUENCE: 43

Thr Leu Thr Thr Asn Glu Glu Tyr Leu Asp Leu Ser Gln
1               5                   10

<210> SEQ ID NO 44
```

```
<211> LENGTH: 13
<212> TYPE: PRT
<213> ORGANISM: Artificial Sequence
<220> FEATURE:
<223> OTHER INFORMATION: Peptide 41_653_665

<400> SEQUENCE: 44

Arg Leu Asp Gly Glu Asn Ile Tyr Ile Arg His Ser Asn
1               5                   10

<210> SEQ ID NO 45
<211> LENGTH: 13
<212> TYPE: PRT
<213> ORGANISM: Artificial Sequence
<220> FEATURE:
<223> OTHER INFORMATION: Peptide RET_1022_1034

<400> SEQUENCE: 45

Thr Pro Ser Asp Ser Leu Ile Tyr Asp Asp Gly Leu Ser
1               5                   10

<210> SEQ ID NO 46
<211> LENGTH: 13
<212> TYPE: PRT
<213> ORGANISM: Artificial Sequence
<220> FEATURE:
<223> OTHER INFORMATION: Peptide ERBB2_1241_1253

<400> SEQUENCE: 46

Pro Thr Ala Glu Asn Pro Glu Tyr Leu Gly Leu Asp Val
1               5                   10

<210> SEQ ID NO 47
<211> LENGTH: 13
<212> TYPE: PRT
<213> ORGANISM: Artificial Sequence
<220> FEATURE:
<223> OTHER INFORMATION: Peptide EPHA7_607_619

<400> SEQUENCE: 47

Thr Tyr Ile Asp Pro Glu Thr Tyr Glu Asp Pro Asn Arg
1               5                   10

<210> SEQ ID NO 48
<211> LENGTH: 13
<212> TYPE: PRT
<213> ORGANISM: Artificial Sequence
<220> FEATURE:
<223> OTHER INFORMATION: Peptide P85A_600_612

<400> SEQUENCE: 48

Asn Glu Asn Thr Glu Asp Gln Tyr Ser Leu Val Glu Asp
1               5                   10

<210> SEQ ID NO 49
<211> LENGTH: 13
<212> TYPE: PRT
<213> ORGANISM: Artificial Sequence
<220> FEATURE:
<223> OTHER INFORMATION: Peptide PDPK1_369_381

<400> SEQUENCE: 49

Asp Glu Asp Cys Tyr Gly Asn Tyr Asp Asn Leu Leu Ser
1               5                   10

<210> SEQ ID NO 50
<211> LENGTH: 13
```

```
<212> TYPE: PRT
<213> ORGANISM: Artificial Sequence
<220> FEATURE:
<223> OTHER INFORMATION: Peptide EFS_246_258

<400> SEQUENCE: 50

Gly Gly Thr Asp Glu Gly Ile Tyr Asp Val Pro Leu Leu
1               5                   10

<210> SEQ ID NO 51
<211> LENGTH: 15
<212> TYPE: PRT
<213> ORGANISM: Artificial Sequence
<220> FEATURE:
<223> OTHER INFORMATION: Peptide ELMO2_706_720

<400> SEQUENCE: 51

Ile Pro Lys Glu Pro Ser Ser Tyr Asp Phe Val Tyr His Tyr Gly
1               5                   10                  15

<210> SEQ ID NO 52
<211> LENGTH: 15
<212> TYPE: PRT
<213> ORGANISM: Artificial Sequence
<220> FEATURE:
<223> OTHER INFORMATION: Peptide Q86W07_1330_1344

<400> SEQUENCE: 52

Gln Val Phe Tyr Asn Ser Glu Tyr Gly Glu Leu Ser Glu Pro Ser
1               5                   10                  15

<210> SEQ ID NO 53
<211> LENGTH: 15
<212> TYPE: PRT
<213> ORGANISM: Artificial Sequence
<220> FEATURE:
<223> OTHER INFORMATION: Peptide P85B_598_612

<400> SEQUENCE: 53

Lys Asn Glu Thr Glu Asp Gln Tyr Ala Leu Met Glu Asp Glu Asp
1               5                   10                  15

<210> SEQ ID NO 54
<211> LENGTH: 15
<212> TYPE: PRT
<213> ORGANISM: Artificial Sequence
<220> FEATURE:
<223> OTHER INFORMATION: Peptide FGD6_747_761

<400> SEQUENCE: 54

Glu Tyr Glu Asn Ile Arg His Tyr Glu Glu Ile Pro Glu Tyr Glu
1               5                   10                  15

<210> SEQ ID NO 55
<211> LENGTH: 15
<212> TYPE: PRT
<213> ORGANISM: Artificial Sequence
<220> FEATURE:
<223> OTHER INFORMATION: Peptide SNX3_15_29

<400> SEQUENCE: 55

Pro Gln Asn Leu Asn Asp Ala Tyr Gly Pro Pro Ser Asn Phe Leu
1               5                   10                  15

<210> SEQ ID NO 56
<211> LENGTH: 15
<212> TYPE: PRT
```

<213> ORGANISM: Artificial Sequence
<220> FEATURE:
<223> OTHER INFORMATION: Peptide SNAG_298_312

<400> SEQUENCE: 56

Thr Ala Ala Asp Glu Glu Glu Asp Glu Tyr Ser Gly Gly Leu Cys
1               5                   10                  15

<210> SEQ ID NO 57
<211> LENGTH: 15
<212> TYPE: PRT
<213> ORGANISM: Artificial Sequence
<220> FEATURE:
<223> OTHER INFORMATION: Peptide IRS2_816_830

<400> SEQUENCE: 57

Cys Gly Gly Asp Ser Asp Gln Tyr Val Leu Met Ser Ser Pro Val
1               5                   10                  15

<210> SEQ ID NO 58
<211> LENGTH: 15
<212> TYPE: PRT
<213> ORGANISM: Artificial Sequence
<220> FEATURE:
<223> OTHER INFORMATION: Peptide ITSN2_960_974

<400> SEQUENCE: 58

Arg Glu Glu Pro Glu Ala Leu Tyr Ala Ala Val Asn Lys Lys Pro
1               5                   10                  15

<210> SEQ ID NO 59
<211> LENGTH: 15
<212> TYPE: PRT
<213> ORGANISM: Artificial Sequence
<220> FEATURE:
<223> OTHER INFORMATION: Peptide ADDB_482_496

<400> SEQUENCE: 59

Pro Asn Gln Phe Val Pro Leu Tyr Thr Asp Pro Gln Glu Val Leu
1               5                   10                  15

<210> SEQ ID NO 60
<211> LENGTH: 15
<212> TYPE: PRT
<213> ORGANISM: Artificial Sequence
<220> FEATURE:
<223> OTHER INFORMATION: Peptide UB713_323_337

<400> SEQUENCE: 60

Cys Pro Phe Ile Asp Asn Thr Tyr Ser Cys Ser Gly Lys Leu Leu
1               5                   10                  15

<210> SEQ ID NO 61
<211> LENGTH: 15
<212> TYPE: PRT
<213> ORGANISM: Artificial Sequence
<220> FEATURE:
<223> OTHER INFORMATION: Peptide CKO59_33_47

<400> SEQUENCE: 61

Leu Asn Gly Ala Glu Pro Asn Tyr His Ser Leu Pro Ser Ala Arg
1               5                   10                  15

<210> SEQ ID NO 62
<211> LENGTH: 15
<212> TYPE: PRT
<213> ORGANISM: Artificial Sequence

```
<220> FEATURE:
<223> OTHER INFORMATION: Peptide MAP1B_1882_1896

<400> SEQUENCE: 62

Pro Asp Glu Glu Asp Tyr Asp Tyr Glu Ser Tyr Glu Lys Thr Thr
1               5                   10                  15

<210> SEQ ID NO 63
<211> LENGTH: 15
<212> TYPE: PRT
<213> ORGANISM: Artificial Sequence
<220> FEATURE:
<223> OTHER INFORMATION: Peptide MALD2_7_21

<400> SEQUENCE: 63

Ser Arg Asn Arg Asp Arg Arg Tyr Asp Glu Val Pro Ser Asp Leu
1               5                   10                  15

<210> SEQ ID NO 64
<211> LENGTH: 15
<212> TYPE: PRT
<213> ORGANISM: Artificial Sequence
<220> FEATURE:
<223> OTHER INFORMATION: Peptide TRXR1_295_309

<400> SEQUENCE: 64

Asn Lys Gly Lys Glu Lys Ile Tyr Ser Ala Glu Arg Phe Leu Ile
1               5                   10                  15

<210> SEQ ID NO 65
<211> LENGTH: 15
<212> TYPE: PRT
<213> ORGANISM: Artificial Sequence
<220> FEATURE:
<223> OTHER INFORMATION: Peptide ACTG_159_173

<400> SEQUENCE: 65

Val Thr His Thr Val Pro Ile Tyr Glu Gly Tyr Ala Leu Pro His
1               5                   10                  15

<210> SEQ ID NO 66
<211> LENGTH: 15
<212> TYPE: PRT
<213> ORGANISM: Artificial Sequence
<220> FEATURE:
<223> OTHER INFORMATION: Peptide SNIP_129_143

<400> SEQUENCE: 66

Ile Tyr Arg Lys Glu Pro Leu Tyr Ala Ala Phe Pro Gly Ser His
1               5                   10                  15

<210> SEQ ID NO 67
<211> LENGTH: 15
<212> TYPE: PRT
<213> ORGANISM: Artificial Sequence
<220> FEATURE:
<223> OTHER INFORMATION: Peptide CBL_667_681

<400> SEQUENCE: 67

Ser Ser Ser Ala Asn Ala Ile Tyr Ser Leu Ala Ala Arg Pro Leu
1               5                   10                  15

<210> SEQ ID NO 68
<211> LENGTH: 15
<212> TYPE: PRT
<213> ORGANISM: Artificial Sequence
<220> FEATURE:
```

-continued

<223> OTHER INFORMATION: Peptide ZNRF3_401_415

<400> SEQUENCE: 68

Arg His Gly Glu Gln Ser Leu Tyr Ser Pro Gln Thr Pro Ala Tyr
1               5                   10                  15

<210> SEQ ID NO 69
<211> LENGTH: 15
<212> TYPE: PRT
<213> ORGANISM: Artificial Sequence
<220> FEATURE:
<223> OTHER INFORMATION: Peptide BCAR1_320_334

<400> SEQUENCE: 69

Pro Leu Leu Arg Glu Glu Thr Tyr Asp Val Pro Pro Ala Phe Ala
1               5                   10                  15

<210> SEQ ID NO 70
<211> LENGTH: 15
<212> TYPE: PRT
<213> ORGANISM: Artificial Sequence
<220> FEATURE:
<223> OTHER INFORMATION: Peptide INT7_928_942

<400> SEQUENCE: 70

Val Lys Ser Leu Glu Asp Pro Tyr Ser Gln Gln Ile Arg Leu Gln
1               5                   10                  15

<210> SEQ ID NO 71
<211> LENGTH: 15
<212> TYPE: PRT
<213> ORGANISM: Artificial Sequence
<220> FEATURE:
<223> OTHER INFORMATION: Peptide FAK1_854_868

<400> SEQUENCE: 71

Pro Ile Gly Asn Gln His Ile Tyr Gln Pro Val Gly Lys Pro Asp
1               5                   10                  15

<210> SEQ ID NO 72
<211> LENGTH: 15
<212> TYPE: PRT
<213> ORGANISM: Artificial Sequence
<220> FEATURE:
<223> OTHER INFORMATION: Peptide DOK1_402_416

<400> SEQUENCE: 72

Tyr Asn Pro Ala Thr Asp Asp Tyr Ala Val Pro Pro Pro Arg Ser
1               5                   10                  15

<210> SEQ ID NO 73
<211> LENGTH: 15
<212> TYPE: PRT
<213> ORGANISM: Artificial Sequence
<220> FEATURE:
<223> OTHER INFORMATION: Peptide CALR3_68_82

<400> SEQUENCE: 73

Thr Thr Gln Asn Gly Arg Phe Tyr Ala Ile Ser Ala Arg Phe Lys
1               5                   10                  15

<210> SEQ ID NO 74
<211> LENGTH: 15
<212> TYPE: PRT
<213> ORGANISM: Artificial Sequence
<220> FEATURE:
<223> OTHER INFORMATION: Peptide HNRPF_299_313

-continued

```
<400> SEQUENCE: 74

Lys Ala Thr Glu Asn Asp Ile Tyr Asn Phe Phe Ser Pro Leu Asn
1               5                   10                  15

<210> SEQ ID NO 75
<211> LENGTH: 15
<212> TYPE: PRT
<213> ORGANISM: Artificial Sequence
<220> FEATURE:
<223> OTHER INFORMATION: Peptide PABP1_357_371

<400> SEQUENCE: 75

Ile Val Ala Thr Lys Pro Leu Tyr Val Ala Leu Ala Gln Arg Lys
1               5                   10                  15

<210> SEQ ID NO 76
<211> LENGTH: 15
<212> TYPE: PRT
<213> ORGANISM: Artificial Sequence
<220> FEATURE:
<223> OTHER INFORMATION: Peptide TWF1_320_334

<400> SEQUENCE: 76

Glu Leu Thr Ala Asp Phe Leu Tyr Glu Glu Val His Pro Lys Gln
1               5                   10                  15

<210> SEQ ID NO 77
<211> LENGTH: 15
<212> TYPE: PRT
<213> ORGANISM: Artificial Sequence
<220> FEATURE:
<223> OTHER INFORMATION: Peptide SPAST_205_219

<400> SEQUENCE: 77

Ser Lys Ser Gln Thr Asp Val Tyr Asn Asp Ser Thr Asn Leu Ala
1               5                   10                  15
```